United States Patent
Melse

(10) Patent No.: US 7,923,865 B2
(45) Date of Patent: Apr. 12, 2011

(54) MULTI-MODE SWITCHED CAPACITOR DC-DC VOLTAGE CONVERTER

(75) Inventor: Abraham Lodewijk Melse, Arnhem (NL)

(73) Assignee: Medtronic, Inc., Minneapolis, MN (US)

( * ) Notice: Subject to any disclaimer, the term of this patent is extended or adjusted under 35 U.S.C. 154(b) by 391 days.

(21) Appl. No.: 12/167,383

(22) Filed: Jul. 3, 2008

(65) Prior Publication Data

US 2009/0326624 A1   Dec. 31, 2009

Related U.S. Application Data

(63) Continuation-in-part of application No. 12/163,724, filed on Jun. 27, 2008, now abandoned.

(51) Int. Cl.
*H02J 1/00* (2006.01)
(52) U.S. Cl. .......................................................... 307/82
(58) Field of Classification Search ................ 307/82
See application file for complete search history.

(56) References Cited

U.S. PATENT DOCUMENTS

| | | | |
|---|---|---|---|
| 4,451,743 A | 5/1984 | Suzuki et al. | |
| 6,084,789 A | 7/2000 | Van Lieshout | |
| 6,198,645 B1 | 3/2001 | Kotowski et al. | |
| 6,563,235 B1 | 5/2003 | McIntyre et al. | |
| 6,799,070 B2 * | 9/2004 | Wolfe et al. ........................ | 607/7 |
| 7,009,849 B2 | 3/2006 | Ramabhadran et al. | |
| 7,180,760 B2 | 2/2007 | Varrichio et al. | |
| 2002/0130705 A1 | 9/2002 | Meng et al. | |
| 2003/0058666 A1 * | 3/2003 | Myono ............................ | 363/59 |
| 2004/0167407 A1 | 8/2004 | Roberts | |
| 2004/0264223 A1 | 12/2004 | Pihlstrom et al. | |
| 2005/0231127 A1 | 10/2005 | Yamamoto et al. | |
| 2008/0061630 A1 * | 3/2008 | Andreu et al. ................ | 307/104 |
| 2008/0074090 A1 | 3/2008 | Darroman | |
| 2008/0150621 A1 | 6/2008 | Lesso et al. | |
| 2008/0239772 A1 * | 10/2008 | Oraw et al. ..................... | 363/60 |

(Continued)

FOREIGN PATENT DOCUMENTS

EP  0 585 925 A2  3/1994

OTHER PUBLICATIONS

Reply to Written Opinion from PCT Application Serial No. PCT/US2008/009024 filed Apr. 26, 2010 (51 pages).

(Continued)

*Primary Examiner* — Robert L. Deberadinis
(74) *Attorney, Agent, or Firm* — Stephen W. Bauer; Michael J. Ostrom

(57) ABSTRACT

The disclosure describes techniques for converting an input voltage level to two or more output voltage levels using only two pump capacitors and three switching phases. The disclosure also describes techniques for selectively controlling a dc-dc converter to operate in different conversion modes. One mode may use only two pump capacitors and three switching phases to produce output voltage levels with a first set of conversion ratios. Another mode may use two pump capacitors and two switching phases to produce output voltage levels with a second set of conversion ratios. The first mode may use three different subcircuit arrangements of the pump capacitors. The second mode may use two different subcircuit arrangements of the pump capacitors. A converter may include switches and pump capacitors that can be selectively configured to transition between two or three different subcircuits, thereby producing output voltages according to different conversion ratios on a selective basis.

41 Claims, 16 Drawing Sheets

U.S. PATENT DOCUMENTS

2009/0278520 A1* 11/2009 Perreault et al. ............. 323/282

OTHER PUBLICATIONS

International Search Report and Written Opinion from PCT Application Serial No. PCT/US2008/009024 mailed Jun. 8, 2009 (21 pages).

Invitation to Pay Additional Fees and, Where Applicable, Protest Fee from PCT Application Serial No. PCT/US2008/009024 mailed Mar. 30, 2009 (4 pages).

D. Maksimovic et al., "Switched-Capacitor DC-DC Converters for Low-Power On-Chip Applications," IEEE Power Electronics Specialists Conference, Jun. 1999, pp. 54-59.

Kester et al., "Switched Capacitor Voltage Converters," Section 4, pp. 4.1-4.21, Analog Devices, Inc, date unknown, downloaded from http://www.analog.com/static/imported-files/seminars_webcasts/76038567ptmsect4.PDF on Jun. 25, 2008.

Maxim Application Note 725, "DC/DC Conversion without Inductors," Maxim Integrated Products, Inc., Nov. 29, 2001.

Tsang et al., Switched Capacitor DC-DC Converters, Topologies and Applications, Presentation, University of California-Berkeley, EE 290, date unknown, downloaded from http://www.ocf.berkeley.edu/~eng/classes/EE290cPresentation.ppt, which indicates last date presentation modified as Mar. 8, 2004.

U.S. Appl. No. 12/167,365, filed Jul. 3, 2008, entitled, "Switched Capacitor DC-DC Voltage Converter".

International Preliminary Report on Patentability from corresponding PCT Application Serial No. PCT/US2008/009024 mailed Oct. 4, 2010 (28 pages).

* cited by examiner

80/60 CONFIGURATION SUBCIRCUITS

83/50 CONFIGURATION
SUBCIRCUITS

FIRST 75/50
CONFIGURATION
SUBCIRCUITS
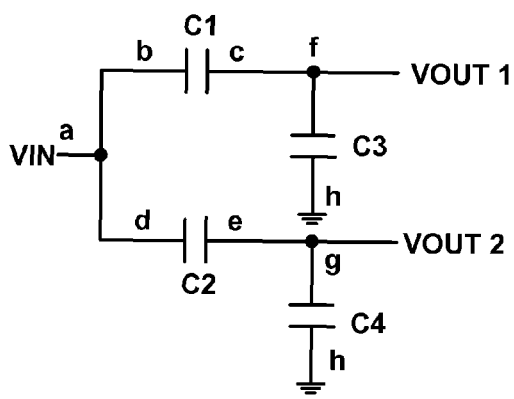
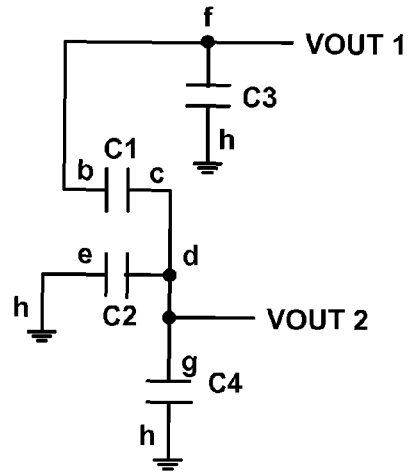
FIG. 11A              FIG. 11B
SECOND 75/50
CONFIGURATION
SUBCIRCUITS
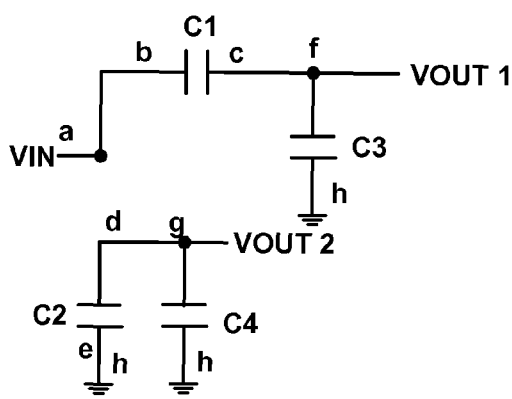
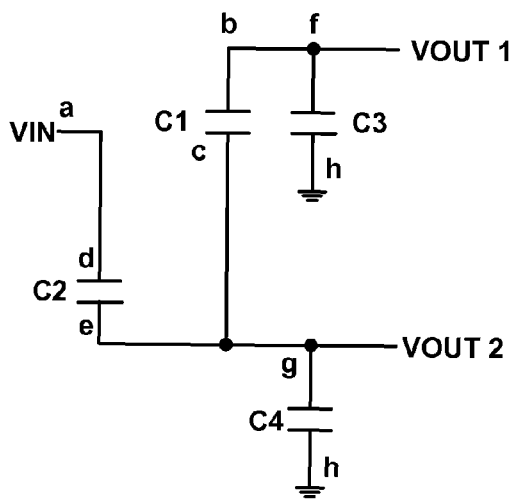
FIG. 12A              FIG. 12B

80/60 CONFIGURATION SUBCIRCUITS FOR A 2 PHASE SOLUTION

MULTI-MODE SWITCHED CAPACITOR DC-DC VOLTAGE CONVERTER

This application is a continuation-in-part of U.S. application Ser. No. 12/163,724, filed Jun. 27, 2008, the entire content of which is incorporated herein by reference.

TECHNICAL FIELD

The disclosure relates to direct current (dc)-dc voltage converters and, more particularly, to switched capacitor dc-dc voltage converters.

BACKGROUND

A dc-dc converter circuit receives a direct current (dc) input voltage from a voltage source at an input level, and converts the input voltage to an output voltage at an output level. The level of the output voltage may be greater than or less than the level of the input voltage. In some cases, the dc-dc converter circuit may produce multiple output voltages at different output levels. The dc-dc converter circuit also converts the input current from the voltage source.

A dc-dc converter circuit may be useful in electrical systems that require multiple operating voltage levels for different electrical devices or circuits within the system. If the system has only one voltage source, such as a battery, for example, a dc-dc converter may convert the level of the voltage source to one or more voltage levels to power a variety of circuits or devices with different operating voltage levels.

One example of a dc-dc converter is a switched capacitor dc-dc converter. In general, a switched capacitor dc-dc converter includes one or more capacitors that are selectively switched across an input and output in charge and pump phases to convert the input voltage level to one or more output voltage levels. The capacitor arrangement and switching configuration may be selected to produce a desired conversion ratio between the input voltage level and output voltage level or levels.

SUMMARY

In general, this disclosure describes techniques for converting a dc input voltage level to two or more dc output voltage levels using only two pump capacitors and three switching phases. In other aspects, the disclosure describes techniques for selectively controlling a dc-dc converter to operate in different conversion modes, providing a multi-mode dc-dc converter. As an example, one mode may use only two pump capacitors and three switching phases to produce output voltage levels with a first set of conversion ratios. Another mode may use two pump capacitors and two switching phases to produce output voltage levels with a second set of conversion ratios.

Consistent with three phases, the first mode may be characterized by three different subcircuit arrangements of the pump capacitors. The second mode may be characterized by two different subcircuit arrangements of the pump capacitors. Hence, as described in this disclosure, a dc-dc converter may include switches and pump capacitors that can be selectively configured to transition between two or three different subcircuits, thereby producing output voltages according to different conversion ratios on a selective basis.

As one example, using two pump capacitors and three switching phases in a first mode, the dc-dc converter may be configured to selectively produce output voltage levels at 80% and 60%, respectively, of an input voltage level. Using two pump capacitors and two switching phases in a second mode, the dc-dc converter may be configured to selectively produce output voltage levels at 75% and 50%, respectively, of an input voltage level. In some aspects, the dc-dc converter may switch between the first and second modes based on a change in the level of the input voltage. In some aspects, the dc-dc converter may switch between the first and second modes based on a change in the level of a load.

In one aspect, the disclosure provides a dc-dc voltage conversion method comprising receiving, at an input node, a dc input voltage at an input level, outputting, at an output node, a dc output voltage at an output level different from the input level, selectively arranging first and second capacitors in at least three different subcircuits relative to the input node and the output node in at least three different phases to convert the dc input voltage at the input level at the input node to the dc output voltage at the output level at the output node, wherein at least one of the subcircuits comprises a subcircuit in which the first and second capacitors are not coupled to the input node.

In another aspect, the disclosure provides a dc-dc voltage conversion device comprising an input node to receive a dc input voltage at an input level, an output node to output a dc output voltage at an output level different from the input level, a first capacitor and a second capacitor, switches configured to selectively arrange the first and second capacitors in at least three different subcircuits relative to the input node and the output node, at least one of the subcircuits comprising a subcircuit in which the first and second capacitors are not coupled to the input node, and a controller configured to control the switches to transition between at least three phases comprising the three different subcircuits to convert the dc input voltage at the input level at the input node to the dc output voltage at the output level at the output node.

In another aspect, the disclosure provides an implantable medical device comprising an implantable medical device housing, medical device circuitry within the housing, a battery, within the housing, that generates a dc input voltage, and a dc-dc voltage conversion device, within the housing, comprising an input node to receive the dc input voltage at an input level, an output node to output a dc output voltage at an output level different from the input level, wherein the dc output voltage provides operating power for at least some of the medical device circuitry, a first capacitor and a second capacitor, switches configured to selectively arrange the first and second capacitors in at least three different subcircuits relative to the input node and the output node, at least one of the subcircuits comprising a subcircuit in which the first and second capacitors are not coupled to the input node, and a controller configured to control the switches to transition between at least three phases comprising the three different subcircuits to convert the dc input voltage at the input level at the input node to the dc output voltage at the output level at the output node.

In another aspect, the disclosure provides a dc-dc voltage conversion device comprising an input node to receive a dc input voltage at an input level, an output node to output a dc output voltage at an output level, a plurality of capacitors, switches configured to selectively arrange the capacitors in different subcircuits relative to the input node and output node, a controller configured to control the switches to transition between a first number of phases comprising a first set of the subcircuits in a first conversion mode, and between a second number of phases comprising a second set of subcircuits in a second conversion mode, to convert the input voltage to the output voltage. The first number is at least three, the output level is different from the input level, and the output level is different in the first and second conversion modes.

In another aspect, the disclosure provides a dc-dc conversion method comprising receiving, at an input node, a dc input voltage at an input level, outputting, at an output node, a dc output voltage at an output level different from the input level, selectively arranging capacitors in different subcircuits relative to the input node and the output node to transition between a first number of phases comprising a first set of the subcircuits in a first conversion mode, and between a second number of phases comprising a second set of subcircuits in a second conversion mode, to convert the input voltage to the output voltage. The first number is at least three, the output level is different from the input level, and the output level is different in the first and second conversion modes.

In another aspect, the disclosure provides an implantable medical device comprising an implantable medical device housing, medical device circuitry within the housing, a battery, within the housing, that generates a dc input voltage, and a dc-dc voltage conversion device, within the housing. The dc-dc voltage conversion device comprises an input node to receive a dc input voltage at an input level, an output node to output a dc output voltage t an output level, a plurality of capacitors, switches configured to selectively arrange the capacitors in different subcircuits relative to the input node and the output node, a controller configured to control the switches to transition between a first number of phases comprising a first set of the subcircuits in a first conversion mode, and between a second number of phases comprising a second set of subcircuits in a second conversion mode, to convert the input voltage to the output voltage. The first number is at least three, the output level is different from the input level, and the output level is different in the first and second conversion modes.

In a further aspect, the disclosure provides a dc-dc voltage conversion method comprising receiving, at an input node, a dc input voltage at an input level, outputting, at a first output node, a first dc output voltage at a first output level, outputting, at a second output node, a second dc output voltage at a second output level, and selectively arranging a set of capacitors consisting essentially of a first capacitor, a second capacitor, and a third capacitor in at least two different subcircuits relative to the input node and the output nodes in two phases comprising the two different subcircuits to convert the dc input voltage at the input level at the input node to the first output voltage at the first output level at the first output node and to the second output voltage at the second output level at the second output node, wherein at least one of the subcircuits comprises a subcircuit in which the first, second, and third capacitors are not coupled to the input node.

In an additional aspect, the disclosure provides a dc-dc voltage conversion device comprising an input node to receive a dc input voltage at an input level, a first output node to output a first dc output voltage at a first output level different from the input level, a second output node to output a second dc output voltage at a second output level different from the input level, a set of capacitors consisting essentially of a first capacitor, a second capacitor, and a third capacitor, switches configured to selectively arrange the set of capacitors in at least two different subcircuits relative to the input node and the output nodes, at least one of the subcircuits comprising a subcircuit in which the first, second, and third capacitors are not coupled to the input node, and a controller configured to control the switches to transition between two phases comprising the two different subcircuits to convert the dc input voltage at the input level at the input node to the first output voltage at the first output level at the first output node and to the second output voltage at the second output level at the second output node.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIGS. 11A and 11B are circuit diagrams illustrating subcircuits for a first switch configuration for a 75%/50% dc-dc converter as shown in FIG. 9.

FIGS. 12A and 12B are circuit diagrams illustrating subcircuits for a second switch configuration for a 75%/50% dc-dc converter as shown in FIG. 10.

DETAILED DESCRIPTION

Figure 1:
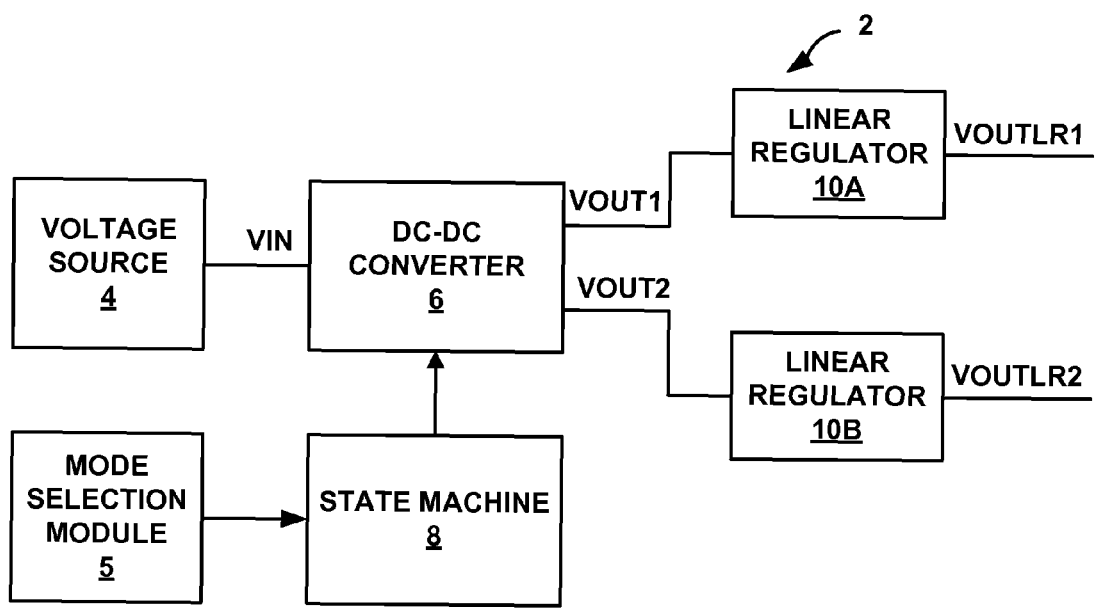
FIG. 1 is a block diagram illustrating an exemplary electrical system including a switched capacitor dc-dc converter.

In many electrical systems, a battery provides operating power to various electrical circuits or devices. Some electrical systems may require operating voltage levels that are greater than the battery voltage. Other electrical systems may require operating voltage levels that are less than the battery voltage. In some cases, an electrical system may require multiple operating voltage levels for different circuits or devices, including multiple voltages that are less than the voltage provided by the battery.

As an example, an implantable medical device such as an implantable electrical stimulation device, sensing device, or therapeutic fluid agent delivery device may include a rechargeable or non-rechargeable battery. If the battery voltage is nominally 3 volts, there may be circuits or devices within the implantable medical devices that require operating voltage levels that are less than 3 volts. As an illustration, in some implantable medical devices, some analog and digital circuits or devices may require different operating voltage levels, such as approximately 1.9 volts for analog circuits or devices and approximately 1.4 volts for some digital circuits or devices.

A dc-dc converters may be used to convert the input voltage to a different voltage to providing operating power for analog and digital circuits or devices. Also, an input current level may be converted to a different output current level. Often, the conversion ratio of a dc-dc converter is fixed. As a result, two dc-dc converters, one to drive digital devices, and another to drive analog devices, may be necessary. Also, a dc-dc converter may only be useful as long as the ratio between the desired output voltage and the input voltage is equivalent to the conversion ratio of the dc-dc converter. Deviation of the input voltage may render the dc-dc converter inoperable or undermine efficiency.

Input voltage deviation commonly occurs in battery driven devices. Over time, as the battery discharges, it may be incapable of providing a constant voltage. In some dc-dc converters, when the battery voltage decreases, the output voltage also may decrease to a point at which the dc-dc converter is no longer capable of driving the analog and digital devices at required levels. Continued operation may require recharging the battery, replacing the battery, or suboptimal operation. Battery replacement in an implanted medical device may a surgical procedure to explant the device.

To accommodate changes in the input voltage, a dc-dc converter may include multiple outputs, where each output is configured with a different conversion ratio. In this manner, as the battery voltage decreases, a different output can be selected. For example, a dc-dc converter may be designed to provide ½, ⅔, and ¾ of the battery voltage. The dc-dc converter may initially provide ½ of the battery voltage. Then, as the battery voltage decreases, the dc-dc converter may provide ⅔ of the battery voltage, and as the battery voltage further decreases, the dc-dc converter may provide ¾ of the battery voltage. In this manner the output voltage is substantially constant, even as the battery voltage reduces. Multiple outputs may require a large number of pump capacitors, however, which may result in a larger circuit area, as well as an increase in the cost of the dc-dc converter.

This disclosure provides techniques for outputting two voltages from a single dc-dc converter, as well as providing multiple conversion ratios, while maintaining or reducing circuit area. Techniques described in this disclosure may provide one or more advantages.

As one example, a dc-dc converter as described in this disclosure may provide two outputs with different conversion ratios providing operating voltage levels for different circuits or devices, such as digital and analog devices requiring different operating levels. In this manner, by providing multiple outputs from a single converter, multiple dc-dc converters may not be needed. For example, a dc input voltage level may be converted to two or more dc output voltage levels. Also, an input current level may be converted to two or more output current levels.

As another example, a dc-dc converter as described in this disclosure may require a reduced circuit area and a reduced number of components, e.g., only two capacitors, to provide a variety of different conversion ratios. In particular, different conversion ratios may be achieved without excessive numbers of capacitors or other components that can increase circuit area and cost. For example, the dc input voltage level may be converted to two or more dc output voltage levels using only two pump capacitors. The use of three switching phases may permit diverse conversion ratios, e.g., 80%/60%, to be achieved with only two pump capacitors.

As a further example, a dc-dc converter as described in this disclosure may be configured to support different conversion modes of operation to accommodate changes in input voltage level. A first mode may use only two pump capacitors and two switching phases to produce output voltage levels with a second set of conversion ratios, e.g., 75%/50%. A first mode may use only two pump capacitors and three switching phases to produce output voltage levels with a first set of conversion ratios, e.g., 80%/60%. When a battery source discharges, for example, a dc-dc converter may transition from a first mode to a second mode to continue to produce desired output levels even though the input voltage level is reduced.

FIG. 1 is a block diagram illustrating an exemplary electrical system 2 comprising a switched capacitor dc-dc converter, in accordance with an aspect of this disclosure. Electrical system 2 may form a power supply for a device or system. In the example of FIG. 1, electrical system 2 includes a voltage source 4, a switched capacitor dc-dc converter 6, and a state machine 8. In some aspects, system 2 also may include a mode selection module 5 and two or more linear regulators 10A and 10B (collectively referred to as linear regulators 10). Voltage source 4 may be any type of device that provides a DC voltage output. For example, voltage source 4 may be a hybrid cathode battery to drive various electrical circuits. System 2 may reside within any of a variety of devices. As an illustration, system 2 may be within an implantable medical device, such as an implantable electrical stimulator, implantable sensing device, or implantable therapeutic fluid agent delivery device.

Examples of implantable electrical stimulators include deep brain stimulators, spinal cord stimulators, pelvic floor stimulators, peripheral nerve stimulators, cochlear stimulators, gastric stimulators, or the like, some of which may be referred to as neurostimulation therapy devices. Other examples of implantable electrical stimulators include implantable pacemakers, cardioverter-defibrillators, or other cardiac therapy devices. Examples of sensing devices include any of a variety of physiological sensing devices for sensing signals, such as cardiac signals, brain signals, accelerometer signals, pressure signals, or the like. Examples of therapeutic agent delivery devices include insulin pumps, intrathecal drug delivery pumps, or the like. Sensing devices may be combined with or cooperatively operate with electrical stimulators or therapeutic fluid agent delivery devices.

Voltage source 4 is coupled to dc-dc converter 6 and provides a DC input voltage, denoted as VIN, to dc-dc converter 6. The dc-dc converter 6 converts the input DC voltage to two output DC voltages, denoted as VOUT1 and VOUT2. VOUT1 and VOUT2 have voltage levels that are respective percentages of the level of the input voltage VIN. The percentages are set by the conversion ratios supported by dc-dc converter 6. The conversion ratio is defined as the output voltage level provided by dc-dc converter 6 at a given output divided by the input voltage level provided by voltage source 4.

The dc-dc converter 6 may comprise a plurality of switches and only two pump capacitors. Each output of the dc-dc converter 6 also may include a respective output capacitor. By toggling the plurality of switches through three switching phases, dc-dc converter 6 provides a plurality of conversion ratios using only two capacitors. The dc-dc converter 6 transitions through three subcircuits in different switching phases to support the conversion ratios associated with the outputs. Each subcircuit is defined by a respective one of the three switching phases. The switches are toggled, i.e., opened and closed, to transition between three switching phases based on a desired conversion ratio, where a first switching phase defines the first subcircuit, a second switching phase defines the second subcircuit, and a third switching phase defines the third subcircuit. During the first switching phase, a first set of the switches are closed. During the second switching phase, a second set of switches are closed. During the third switching phase, a third set of switches are closed. At least some of the switches closed in the first, second and third switching phases are different, such that the first, second and third switching phases form different subcircuits.

By using different switching schemes, dc-dc converter 6 provides a plurality of conversion ratios using only two capacitors and three switching phases. Different switching schemes may be employed to generate different subcircuits. Toggling between the subcircuits, i.e., toggling between switching phases, generates output voltages at various levels. For example, in one embodiment, the switches may be configured to toggle between the three switching phases such that VOUT1 is 80% of VIN and VOUT2 is 60% of VIN. In another embodiment, the switches may be configured to toggle between the three switching phases such that VOUT1 is 67% of VIN and VOUT2 is 50% of VIN. It is important to reiterate that the different output levels, i.e., conversion ratios, are generated with only two capacitors that are charged and pumped by toggling between three switching phases. In this manner, the pump capacitors consist of only two pump capacitors, which are switched through to form three different subcircuits relative to VIN, VOUT1 and VOUT2.

State machine 8 forms a controller that controls various switches within dc-dc converter 6. In particular, state machine 8 is coupled to dc-dc converter 6 and provides a signal to control the state, i.e., open or closed, of the various switches within dc-dc converter 6. For example, state machine 8 may output a signal to toggle the first set of switches to transition to the first switch phase. State machine 8 may then output a signal to toggle the second set of switches to transition to the second switch phase. Finally, state machine 8 may output a signal to toggle the third set of switches to transition to the third switch phase. State machine 8 may continuously repeat these steps. As another example, state machine 8 may output a serial data stream to dc-dc converter 6 that defines which switches need to be toggled and in what order. In response, dc-dc converter 6 may toggle the specified switches in the specified order.

In some embodiments, system 2 includes mode selection module 5, which may support multi-mode operation of dc-dc converter 6. Mode selection module 5 is coupled to state machine 8 and transmits a signal to state machine 8 that defines the conversion ratio. As one example, mode selection module 5 may store a list of possible conversion ratios and assign a binary string to each conversion ratio. Mode selection module 5 may transmit the binary string to state machine 8. State machine 8 may also store a list of possible conversion ratios and store the binary string associated with each conversion ratio. After receiving the binary string from mode selection module 5, state machine 8 may query the stored list to determine the desired conversion ratio and selectively toggle the switches within dc-dc converter 6 to produce the desired conversion ratio. Transmitting a binary string to define the conversion ratio is just one example. Other techniques may also be used to define the conversion ratio.

For clarity, the following is one example of the operation of mode selection module 5. Mode selection module 5 transmits a signal to state machine 8 that causes state machine 8 to toggle the switches within dc-dc converter 6 between the three switching phases to generate outputs that are at 67% and 50% of the input voltage, i.e., VOUT1 equals 0.67*VIN and VOUT2 equals 0.5*VIN. Subsequently, due to either internal processing within mode selection module 5 or alternatively, due to an external input, mode selection module 5 transmits a signal to state machine 8 that causes state machine 8 to toggle the switches within dc-dc converter 6 between the three switching phases to generate outputs that are at 80% and 60% of the input voltage, i.e., VOUT1 equals 0.8*VIN and VOUT2 equals 0.6*VIN. In this manner, dc-dc converter 6 transitions from a three-phase 67%/50% conversion mode to a three-phase 80%/60% conversion mode.

As another example, mode selection module 5 may cause state machine 8 to control dc-dc converter 6 to operate in a first mode with a conversion ratio of 75%/50% and a second mode with a conversion ratio of 80%/60%. Mode selection module 5 may cause a transition from the first mode to the second mode when the input voltage level changes by a predetermined amount. For example, voltage source 4 may be formed by a battery that depletes over time such that the input voltage level is reduced over time.

Mode selection module 5 may include one or more comparators that compare the input voltage level to respective threshold voltage levels. In some implementations, mode selection module 5 may compare one or more output load levels to threshold load levels to determine whether to select a different conversion ratio mode.

As an example of switching modes in response to changes in input voltage level, if the input voltage level drops below a given threshold voltage level, mode selection module 5 may control state machine 8 to transition from a lower conversion ratio to a higher conversion ratio, e.g., from 75%/50% to 80%/60%. In this manner, by producing an output voltage level as a higher percent of the input voltage level, the output voltage level may be more effectively maintained as the input voltage level decreases, e.g., due to battery discharge over time.

In some embodiments, system 2 includes linear regulators 10. Linear regulators 10 may be any type of linear regulators. Linear regulators 10 further filter the output voltages, VOUT1 and VOUT2, to generate a smoother DC output voltage. In one example, each of linear regulators 10 may be a simple resistor-capacitor (RC) filter. In other examples, linear regulators 10 may be realized by active voltage regulation circuitry or a combination of passive and active voltage regulation circuitry.

Figure 2:
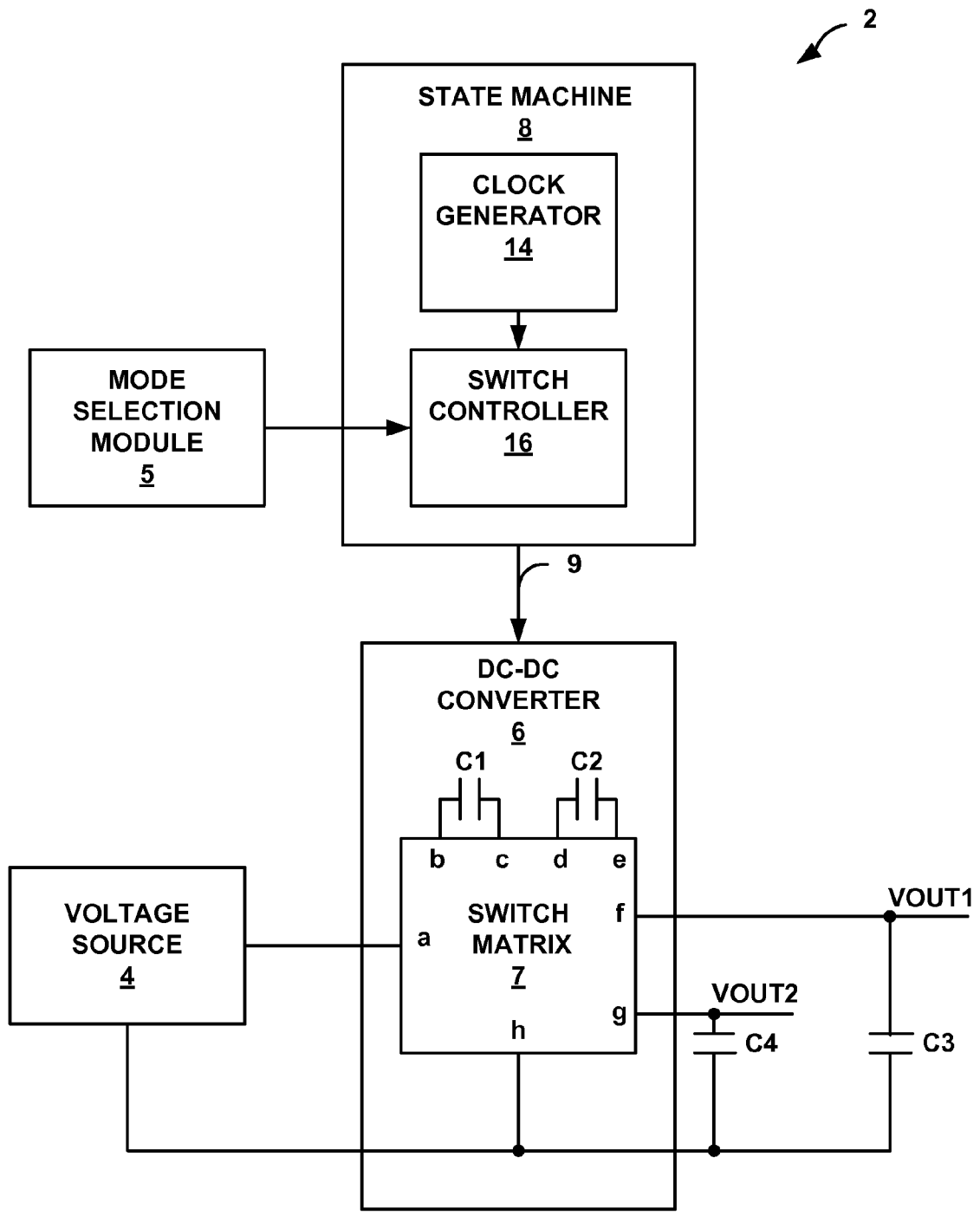
FIG. 2 is a block diagram illustrating the exemplary electrical system of FIG. 1 in more detail.

FIG. 2 is a block diagram illustrating the exemplary electrical system 2 of FIG. 1 in more detail. As shown in FIG. 2, state machine 8 includes clock generator 14 and switch controller 16. Switch controller 16 transmits a signal via line 9 to dc-dc converter 6 that defines which switches within dc-dc converter 6 need to be closed or open at a given time, i.e., in a given phase of a switching cycle. In one example, switch controller 16 transmits a serial data stream via line 9 to dc-dc converter 6 that defines the switches that need to be toggled. The dc-dc converter 6 may include a processor (not shown)

that receives the serial data stream and, in response, toggles the switches defined by switch controller 16. In another example, line 9 may be a plurality of parallel lines, each of which is connected to the plurality of switches within dc-dc converter 6. In such an example, switch controller 16 transmits a binary value via the line 9 that causes the desired switches to close and the other switches to open.

Switch controller 16 may transmit either a serial data stream or parallel binary values every rising or falling edge of a periodic wave generated by clock generator 14. Clock generator 14 may be any device capable of outputting a periodic wave such as a sine wave, a triangle wave, or a square wave to name a few examples. In one example, the frequency of the periodic wave is 8 kHz. The periodic wave clocks the output of switch controller 16. For example, on a first rising edge of the periodic wave, switch controller 16 may transmit a signal that causes a first set of switches to close and generate the subcircuit of the first switch phase. On a second rising edge of the periodic wave, switch controller 16 may transmit a signal that causes a second set of switches to close and generate the subcircuit of the second switch phase. On a third rising edge of the periodic wave, switch controller 16 may transmit a signal that causes a third set of switches to toggle and generate the subcircuit of the third switch phase. Switch controller 16 may repeat these steps for every rising edge of the periodic wave provided by clock generator 14. Similarly, switch controller 16 may transmit a signal every falling edge of the periodic wave.

As shown in FIG. 2, dc-dc converter 6 includes switch matrix 7 and pump capacitors C1 and C2. As shown in FIG. 2, capacitors C1 and C2 are external to switch matrix 7; however, in some embodiments, capacitors C1 and C2 may be internal to switch matrix 7. A dc-dc converter 6 may be constructed using any of a variety of process technologies. As an example, switches forming switch matrix 7 may be formed, in some implementations, by MOSFET devices formed on a chip in a 0.8 micron process.

Switch matrix 7 includes a plurality of switches to interconnect nodes a-h. Voltage source 4 is coupled to node a of switch matrix 7. Node a may be considered to be an input node that receives dc input voltage at an input level. Node h provides a common reference. In some embodiments, node h may be connected directly to a common ground. A first capacitor C1 is coupled between nodes b and c, and a second capacitor C2 is coupled between nodes d and e. Node f provides a first voltage output, VOUT1, and node g provides a second voltage output, VOUT2. Node f may be considered to be a first output node that outputs a dc output voltage at an output level different than the input level. Node g may be considered to be a second output node that outputs a dc output voltage at an output level different than the input level and different than the output level of the output voltage at node f. Additionally, as shown in FIG. 2, a third capacitor, output capacitor C3, is coupled between VOUT1 and the common reference, e.g., a ground potential, and a fourth capacitor, output capacitor C4, is coupled between VOUT2 and the common reference. The voltage VOUT1 is generated across capacitor C3, and voltage VOUT2 is generated across capacitor C4. In general, capacitors C1 and C2 may be referred to as pump capacitors and capacitors C3 and C4 may be referred to as output or buffer capacitors.

The plurality of switches within switch matrix 7 may interconnect nodes a-h in various combinations to transition between the three switching phases. In addition, the plurality of switches may interconnect nodes a-h to generate various conversion ratios. Table 1 defines the interconnection between nodes a-h for different switching phases, as well as, interconnection between nodes a-h for various conversion ratios.

In response to control signals from switch controller 16, such as parallel or serial control words, switch matrix 7 selectively opens and closes various switches to produce specified combinations of interconnections between nodes a-h for different switch phases, and thereby realize different conversion modes and conversion ratios.

Switch controller 16 may drive the switch phases, e.g., first switch phase, second switch phase, and third switch phase, in a substantially continuous progression in response to clock signals generated by clock generator 14. Switch matrix may comprise any of a variety of different switching devices, such as field effect transistors (FETs) having gates that received control signals to open and close the transistors.

In Table 1 below, letter notation indicates nodes that are electrically interconnected together in a given conversion mode and switch phase. For example, in the first switch phase for the 80%/60% mode, the notation "abd, cf, ef" means: the nodes 'a,' 'b,' and 'd' are connected together in switch matrix 7, nodes 'c' and 'f' are connected together, and nodes 'e' and 'g' are connected together in switch matrix 7. No other connections are made in switch matrix 7 in the first switch phase of the 80%/60% mode. The arrangement of nodes a-h relative to voltage source 4 (VIN), pump capacitor C1, pump capacitor C2, output capacitor C3 (VOUT1) and output capacitor C4 (VOUT2), and a ground or reference voltage will be described in further detail with reference to FIG. 3 below.

TABLE 1

| dc-dc converter mode | Nodes that are interconnected with one another within switch matrix 7 | | | Conversion Ratio VOUT1/VIN | Conversion Ratio VOUT2/VIN |
|---|---|---|---|---|---|
| | First Switch Phase | Second Switch Phase | Third Switch Phase | | |
| 80%/60% | abd, cf, eg | ad, bf, ceg | bg, cd, eh | 0.8 | 0.6 |
| 83%/50% | ab, cdf, eg | ad, bf, ce | bg, cd, eh | 0.833 | 0.5 |
| 67%/50% | ad, bef, cg | bd, cf, eg | bg, cd, eh | 0.667 | 0.5 |
| 80%/40% | abd, cef | bf, cd, eg | bg, cd, eh | 0.8 | 0.4 |
| 75%/25% | ab, cdf, eg | bd, cg, eh | beg, ch, df | 0.75 | 0.25 |
| 75%/25% | ab, cdf, eg | ad, bf, ce | beg, ch, df | 0.75 | 0.25 |
| 60%/40% | ad, bef, cg | bd, cf, eg | bf, cdg, eh | 0.6 | 0.4 |
| 60%/40% | ab, cd, ef | bdf, ceg | bg, cd, eh | 0.6 | 0.4 |
| 60%/20% | ab, cd, ef | bf, cd, eg | bdg, ceh | 0.6 | 0.2 |
| 50%/33% | ab, cd, ef | bd, cf, eg | bf, cdg, eh | 0.5 | 0.333 |
| 50%/17% | ab, cd, ef | beg, ch, df | bd, cg, eh | 0.5 | 0.167 |
| 40%/20% | ab, cd, ef | bdf, cg, eh | bg, ceh, df | 0.4 | 0.2 |

As can be ascertained by Table 1, switch controller 16 controls the switches within switch matrix 7 to transition between the at least three phases in response to a clock signal generated by clock generator 14 such that a ratio x defined as VOUT1/VIN and a ratio y defined as VOUT2/VIN, represented as a percentage value, is one of x/y equal to approximately 80%/60%, 83%/50%, 67%/50%, 80%/40%, 75%/25%, 60%/40%, 60%/20%, 50%/33%, 50%/17%, or 40%/20%. For example, in one aspect, mode selection module 5 selects one of the plurality of conversion modes by transmitting a signal to state machine 8 that defines the dc-dc conversion mode, e.g., the dc-dc conversion mode is 80%/60%. In response, upon a rising edge of the periodic wave provided by clock generator 14, switch controller 16 transmits a signal to dc-dc converter 6 to toggle, i.e., open or close, a first set of the plurality of switches within switch matrix 7 to interconnect nodes a, b, and d, nodes c and f, and nodes e and g. This generates the subcircuit associated with the first switch phase. Upon the next rising edge, switch controller 16 transmits a signal to dc-dc converter 6 to toggle a second set of the plurality of switches to interconnect nodes a and d, nodes b and f, and nodes c, e, and g. This generates the subcircuit associated with the second switch phase. Upon the following rising edge, switch controller 16 transmits a signal to dc-dc converter 6 to toggle a third set of the plurality of switches to interconnect nodes b and g, nodes c and d, and nodes e and h. This generates the subcircuit associated with the third switch phase. Notably, none of the subcircuits associated with the third switch phase require a connection to node a (VIN). In each subcircuit in the third switch phase illustrated in Table 1, capacitors C1 and C2 are not coupled to the input voltage VIN at the input node.

Generally, switch controller 16 is configured to control the switches within switch matrix 7 to form different sets of the subcircuits based on the selected conversion mode. In one non-limiting example, each of the subcircuit configurations comprises a set of capacitors consisting essentially of the first and second capacitors, i.e., capacitors C1 and C2, and in some examples may also include capacitors C3 and C4. Along with capacitors C1, C2, C3 and C4, each of the subcircuits may require substantially no additional components other than the switches. In some examples, each subcircuit may consist of, or consist essentially of pump capacitors C1 and C2, output capacitors C3 and C4, and the switches, arranged between VIN at the input node and one or more voltages VOUT1 an VOUT2 at one or more output nodes. The subcircuits may consist essentially of pump capacitors C1 and C2 in the sense that substantially no additional pump capacitors are included in a manner that would contribute in a substantial way to voltage conversion.

In a first implementation, dc-dc converter 6 repeatedly transitions from the first switch phase, to the second switch phase, then to the third switch phase, and back to the first phase. However, the techniques described in this disclosure are not so limited. In a second implementation, dc-dc converter 6 may transition from the first switch phase to the third switch phase then to the second switch phase and back to the first switch phase. Second order characteristics such as output resistance of the dc-dc converter 6 may be different in the two implementations, and as explained in more detail below the second order characteristics may be better for the first implementation.

Although Table 1 shows numerous dc-dc conversion modes for purposes of illustration, only one or a few of the dc-dc conversion modes may actually be provided within dc-dc converter 6. In some implementations, switch matrix 7 may be designed with switches for only one conversion mode, and may not have the necessary switches for any of the other conversion modes shown in Table 1. For example, switch matrix 7 may be constructed to only include switches for the 80%/60% conversion mode. In such implementations, mode selection module 5 may not be necessary. In other implementations, switch matrix 7 may only include switches arranged to provide a subset of the dc-dc conversion modes described in Table 1. For example, switch matrix 7 may only include switches to provide conversion ratios of 80%/60% and 67%/50%.

Additionally, as shown in Table 1 and in FIG. 2, dc-dc converter 6 provides two output nodes. Node f may be considered to be a first output node, and node g may be considered to be a second output node. However, in some implementations, one of the output nodes (f or g) may not be necessary, and only one output node may be necessary. In such an implementation, either node f or g may be an output node, instead of a first output node and a second output node.

As shown in FIG. 2, VIN is coupled to node a, VOUT1 is coupled to node f, and VOUT2 is coupled to node g. In such instances, dc-dc converter 6 functions as a down converter, i.e., VOUT1 and VOUT2 are less than VIN. However, various aspects of the disclosure are not so limited. In some embodiments, voltage source 4 (VIN) may be coupled to node f or g, and VOUT1 or VOUT2 may be coupled to node a. In such embodiments, dc-dc converter 6 functions as an up converter, i.e., VOUT1 or VOUT2 is greater than VIN. For example, in one embodiment, voltage source 4 is coupled to node f, VOUT1 is coupled to node a, capacitor C3 is coupled between node a (VOUT1) and node h, and VOUT2 is coupled to node g.

Assume switches within dc-dc converter 6 are configured for the 80%/60% conversion mode as described in Table 1. If VIN is coupled to node f and VOUT1 is coupled to node a, then VIN/VOUT1 equals 0.8. Therefore, the conversion ratio VOUT1/VIN equals 1.25. In this example, dc-dc converter 6 functions as an up converter since VOUT1 is greater than VIN. VOUT2/VIN would be 0.75 in this example. When dc-dc converter 6 is configured as an up converter, where node f is the input node, VOUT1 is coupled to node a, and VOUT2 is coupled to node g, the conversion ratio for the VOUT2 output (VOUT2/VIN) can be considered to be the ratio of the conversion ratios if dc-dc converter 6 is configured as a down converter. Simply put, if dc-dc converter 6 is configured as an up converter with switches configured for the 80%/60% conversion mode described in Table 1 and VOUT1 is coupled to node a, and VOUT2 is coupled to node g, then the conversion ratio for VOUT2 is the conversion ratio for VOUT2 divided by the conversion ratio for VOUT1 as described in Table 1. Therefore, in the example up converter above, VOUT2/VIN equals 0.75, i.e., 0.6/0.8, per the conversion factors of Table 1.

If VIN is coupled to node g and VOUT2 is coupled to node a, then VIN/VOUT2 equals 0.6. Therefore, the conversion ratio VOUT2/VIN substantially equals 1.67. If dc-dc converter 6 is configured as an up converter with switches configured for the 80%/60% conversion mode described in Table 1 and VOUT2 is coupled to node a, and VOUT1 is coupled to node f, then the conversion ratio for VOUT1 is the conversion ratio for VOUT1 divided by the conversion ratio for VOUT2 as described in Table 1. VOUT1/VIN would be substantially equal to 1.33, i.e., 0.8/0.6, because in Table 1 the conversion ratio for VOUT1 is 0.8, and the conversion ratio for VOUT2 is 0.6.

Similarly, if the switches within dc-dc converter 6 are configured for the 60%/40% conversion mode, and VIN is coupled to node f and VOUT1 is coupled to node a, then VIN/VOUT1 equals 0.6. Stated another way, the conversion ratio, VOUT1/VIN substantially equals 1.67. The conversion ratio VOUT2/VIN substantially equals 0.67, i.e., 0.4/0.6. If VIN is coupled to node g and VOUT2 is coupled to node a, then VIN/VOUT2 equals 0.4. Therefore, the conversion ratio VOUT2/VIN equals 2.5. The conversion ratio VOUT1/VIN substantially equals 1.5, i.e., 0.6/0.4. In general, nodes a, f, and g may be considered to be three equivalent nodes in the sense that voltage source 4 may be coupled to any one of nodes a, f, or g. VOUT1 or VOUT2 may be coupled to node a, with capacitors C3 coupled between VOUT1 and node h, and capacitor C4 coupled between VOUT2 and node h.

While dc-dc converter 6 may be configured as an up converter or a down converter, for ease of illustration and purposes of example, dc-dc converter 6 will be described as a down converter. Stated otherwise, in the embodiments described below, VIN is coupled to node a, VOUT1 is coupled to node f, and VOUT2 is coupled to node g.

Figure 3:
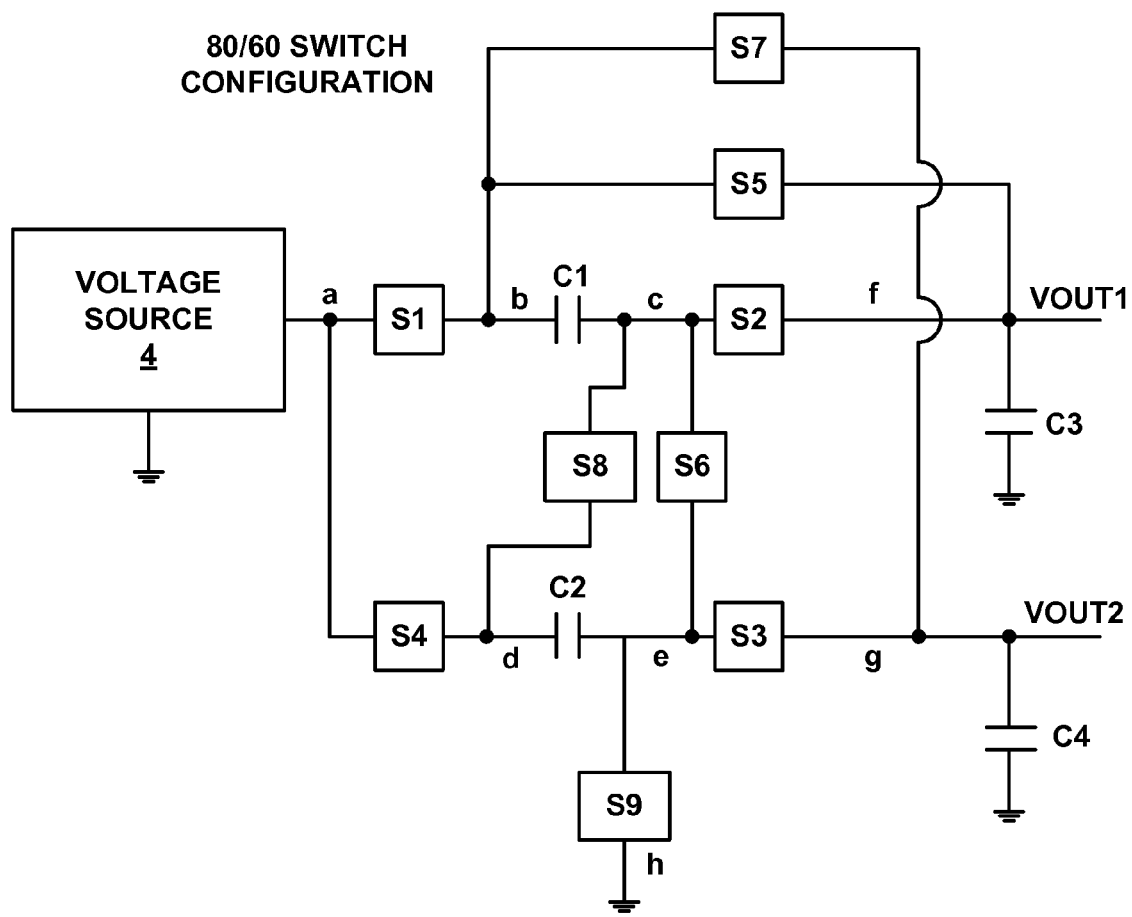
FIG. 3 is a circuit diagram illustrating a switch configuration for the dc-dc converter of FIG. 1 configured for an 80%/60% conversion ratio mode.

FIG. 3 is a circuit diagram illustrating a switch configuration for dc-dc converter 6 configured for an 80%/60% conversion ratio mode, i.e., a mode in which, approximately, VOUT1=0.8×VIN and VOUT2=0.6×VIN. As shown in FIG. 3, for the 80%/60% mode, switch matrix 7 includes switches S1-S9. Switches S1-S9 may be MOSFET switches with approximately 20 ohms of on-resistance. In different implementations, switches S1-S9 may be formed by other types of switches and the on-resistance may be greater or less than approximately 20 ohms.

In the example of FIG. 3, voltage source 4 is coupled between ground and node a to provide an input voltage VIN at node a. Switch S1 is electrically coupled between node a and node b, switch S2 is coupled between node c and node f (VOUT1), switch S3 is coupled between node e and g (VOUT2), switch S4 is coupled between node a and node d, switch S5 is coupled between node b and node f (VOUT1), switch S6 is coupled between node c and node e, switch S7 is coupled between nodes b and g (VOUT2), switch S8 is coupled between nodes c and d, switch S9 is coupled between node e and node h (ground), pump capacitor C1 is coupled between nodes b and c, pump capacitor C2 is coupled between nodes d and e, output capacitor C3 is coupled between node f (VOUT1) and ground, and output capacitor C4 is coupled between node g (VOUT2) and ground.

Figure 6A:
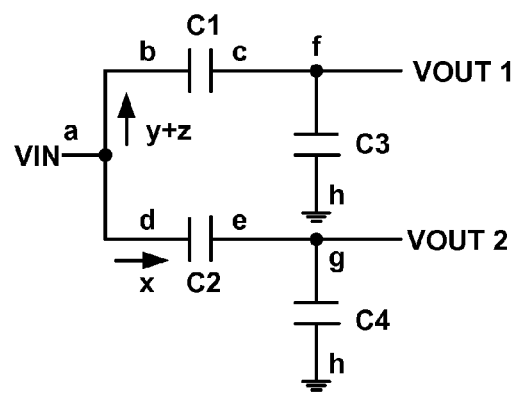
FIGS. 6A-6C are circuit diagrams illustrating subcircuits for the dc-dc converter of FIG. 1 configured for the 80%/60% conversion ratio mode.
Figure 6B:
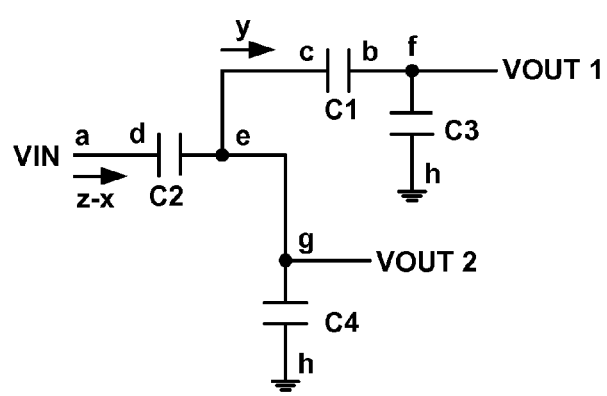
Figure 6C:
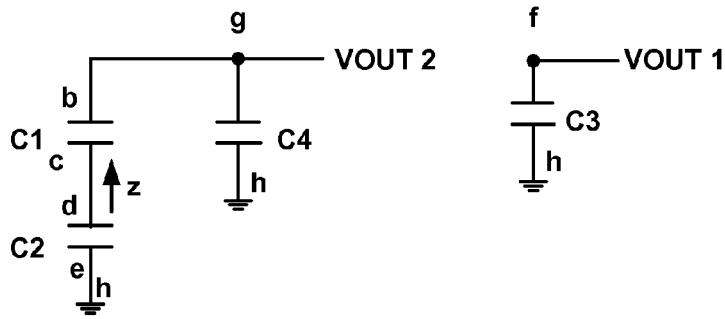

As presented in Table 1, for the first switch phase, nodes a, b, and d are connected together, e.g., by closing switches S1 and S4, nodes c and f are connected together, e.g., by closing switch S2, and nodes e and g are connected together, e.g., by closing switch S3. Hence, for the first switch phase, nodes a, b, and d are connected together by toggling ON switches S1 and S4. Toggling ON means that the switch is driven so that current can flow through the switch, such that the switch, in effect, closes. Nodes c and f are connected together by toggling ON switch S2, and nodes e and g are connected together by toggling ON switch S3. Switches S5-S9 are left open in the first switch phase of the switching cycle such that no current can flow through them. Switches S1-S4 are the first set of switches that are toggled ON by switch controller 16 to transition to the first switch phase. Toggling ON only switches S1-S4 generates the subcircuit associated with the first switch phase for the 80%/60% mode, as shown in FIG. 6A. Examples of subcircuits corresponding to the first switch phase, second switch phase, and third switch phase are shown in FIGS. 6A-6C.

For the second switch phase, nodes a and d are connected together, nodes b and f are connected together, and nodes c, e, and g are connected together. For the second switch phase, nodes a and d are connected together by toggling ON switch S4. Nodes b and f are connected together by toggling ON switch S5. Nodes c, e, and g are connected together by toggling ON switch S6 and S3. All other switches are left open or toggled OFF if they were ON in the first switch phase such that they are now open in the second switch phase. Switches S3-S6 are the second set of switches that are toggled ON by switch controller 16 to transition to the second switch phase from the first switch phase. Switch controller 16 toggles OFF switches S1 and S2 that were previously toggled on during the first switch phase. Toggling ON only switches S3-S6 generates the subcircuit associated with the second switch phase for the 80%/60% mode, as shown in FIG. 6B.

For the third switch phase, nodes b and g are connected together, nodes c and d are connected together, and nodes e and h are connected together. For the third switch phase, nodes b and g are connected together by toggling ON switch S7. Nodes c and d are connected together by toggling ON switch S8. Nodes e and h are connected together by toggling ON switch S9. All other switches are left open. Switches S7-S9 are the third set of switches that are toggled on by switch controller 16 to transition to the third switch phase from the second switch phase. Switch controller 16 toggles OFF switches S3-S6 that were previously toggled ON during the second switch phase. Toggling ON only switches S7-S9 generates the subcircuit associated with the third switch phase for the 80%/60% mode, as shown in FIG. 6C. Neither capacitor C1 nor C2 is coupled to the input node, node a, in the subcircuit associated with the third switch phase.

To summarize, switch controller 16 outputs a signal to dc-dc converter 6 that causes switch matrix 7 of dc-dc converter 6 to toggle ON and OFF various switches within dc-dc converter 6. For the 80%/60% mode, on a rising or falling edge of the periodic wave generated by clock generator 14, switch controller 16 outputs a signal to dc-dc converter 6 to toggle ON switches S1-S4, and toggle OFF all other switches. This transitions dc-dc converter 6 to the first switch phase. Upon the next rising or falling edge of the periodic wave, switch controller 16 outputs a signal to dc-dc converter 6 to toggle OFF switches S1-S2, and toggle ON switches S3-S6. This transitions dc-dc converter 6 from the first switch phase to the second switch phase. Upon the next rising or falling edge, switch controller 16 outputs a signal to dc-dc converter to toggle OFF switches S3-S6, and toggle ON switches S7-S9. This transitions dc-dc converter 6 from the second switch phase to the third switch phase. By continuously transitioning through the three phases (first, second, and third switch phases), in steady state, VOUT1 equals the voltage at node a (VIN) multiplied by approximately 0.8, and VOUT2 equals VIN multiplied by approximately 0.6, as explained in more detail with respect to FIGS. 6A-6C.

Stated another way, switch matrix 7 includes a plurality of switches configured to selectively arrange the first and second capacitors, i.e., capacitor C1 and C2, in at least three different subcircuits. Switch controller 16 controls the switches within switch matrix 7 to transition between at least three phases (first switch phase, second switch phase, and third switch phase) comprising the three different subcircuits to convert the input voltage at node a to the output voltage at nodes f and g.

Figure 4A:
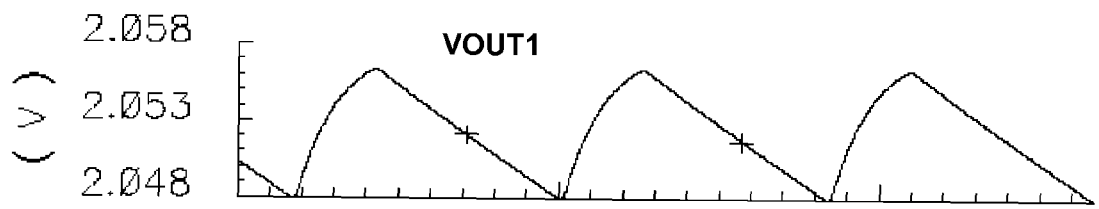
FIGS. 4A and 4B are exemplary time versus amplitude plots for outputs of the dc-dc converter of FIG. 1 configured for the 80%/60% conversion ratio mode with a certain load at the outputs.
Figure 4B:
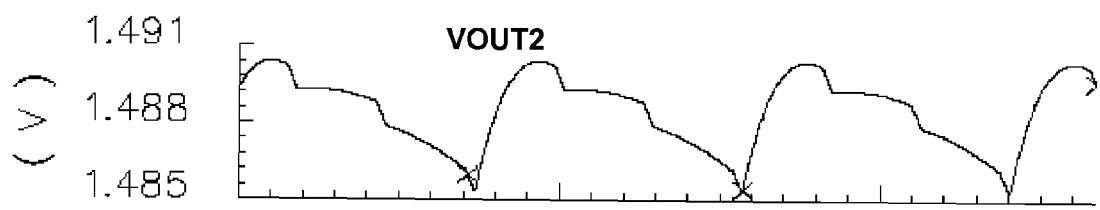

FIGS. 4A and 4B are exemplary time versus amplitude plots for outputs of dc-dc converter 6 configured for the 80%/60% mode with output loading. FIG. 4A shows the time versus amplitude plot for VOUT1. FIG. 4B shows the time versus amplitude plot for VOUT2. In FIGS. 4A and 4B, VIN is 2.65V. In FIG. 4A, VOUT1 is represented as being loaded by 0.5 milliamps (mA). In FIG. 4B, VOUT2 is represented as being loaded by 1 mA. The 0.5 mA and 1 mA loading cause VOUT1 and VOUT2 to be less than ideal. For example, the ideal value of VOUT2 is 2.65V multiplied by 0.6 which equals 1.59V. However, as shown in FIG. 4B, at its peak, VOUT2 equals 1.49V. In FIG. 4B, VOUT2 is not at its ideal value because of the output resistance at VOUT2. In FIG. 4B, the output resistance (ROUT2) at VOUT2 is approximately 100 ohms. Therefore, the loading current flowing through ROUT2 reduced VOUT2 from its ideal value by 0.1V. Stated another way, the actual value of VOUT2 can be calculated by subtracting the voltage drop caused by ROUT2 from the ideal value of VOUT2, i.e., 1.59V−(1 mA)(100 ohms)=1.49V.

Figure 4C:
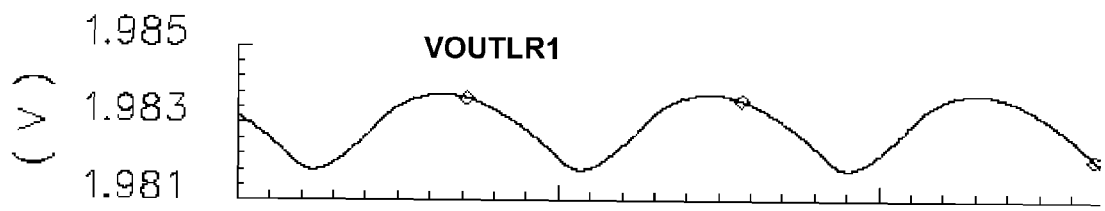
FIGS. 4C and 4D are exemplary time versus amplitude plots for outputs of linear regulators coupled to the dc-dc converter configured for the 80%/60% conversion ratio mode.
Figure 4D:
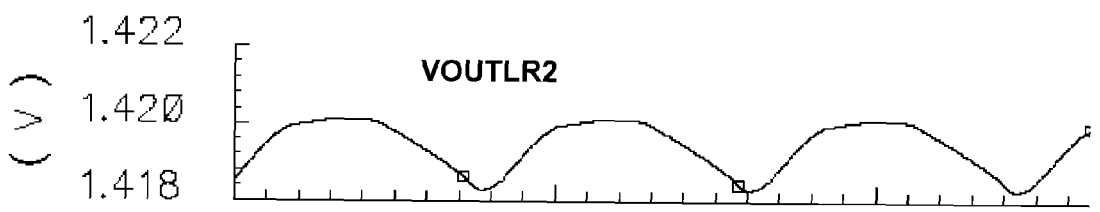

FIGS. 4C and 4D are exemplary time versus amplitude plots for outputs VOUTLR1 and VOUTLR2 of linear regulators 10 coupled to the dc-dc converter 6 configured for the 80%/60% mode. As described above, one example of a linear regulator 10 is a simple, passive resistor-capacitor low pass filter that smoothes the respective output signal VOUT1 or VOUT2. In other implementations, a linear regulator 10 may include active circuitry or combinations of active and passive circuitry to produce the regulated output voltages VOUTLR1 and VOUTLR2. As shown in FIG. 4C, linear regulator 10A filters VOUT1 to remove high frequency components and produce a smoother voltage output VOUTLR1. Similarly, as shown in FIG. 4D, linear regulator 10B filters VOUT2 to remove high frequency components and produce a smoother voltage output VOUTLR2.

The VOUTLR1 and VOUTLR2 voltage levels shown in FIGS. 4C and 4D may be used to drive different circuits or devices within system 2. For example, VOUTLR1 may be used to drive some analog or digital circuits or devices. VOUTLR2 may be used to drive other digital circuits or devices. As an illustration, VOUTLR1 could provide operating voltage for various analog circuitry and digital logic devices, while the lower VOUTLR2 could provide operating voltage for a microprocessor, digital signal processor, or logic core that requires a lower operating voltage than the analog circuitry and other digital logic devices, such as logic devices formed in an application specific integrated circuit (ASIC) or field programmable gate array (FPGA).

Figure 5:
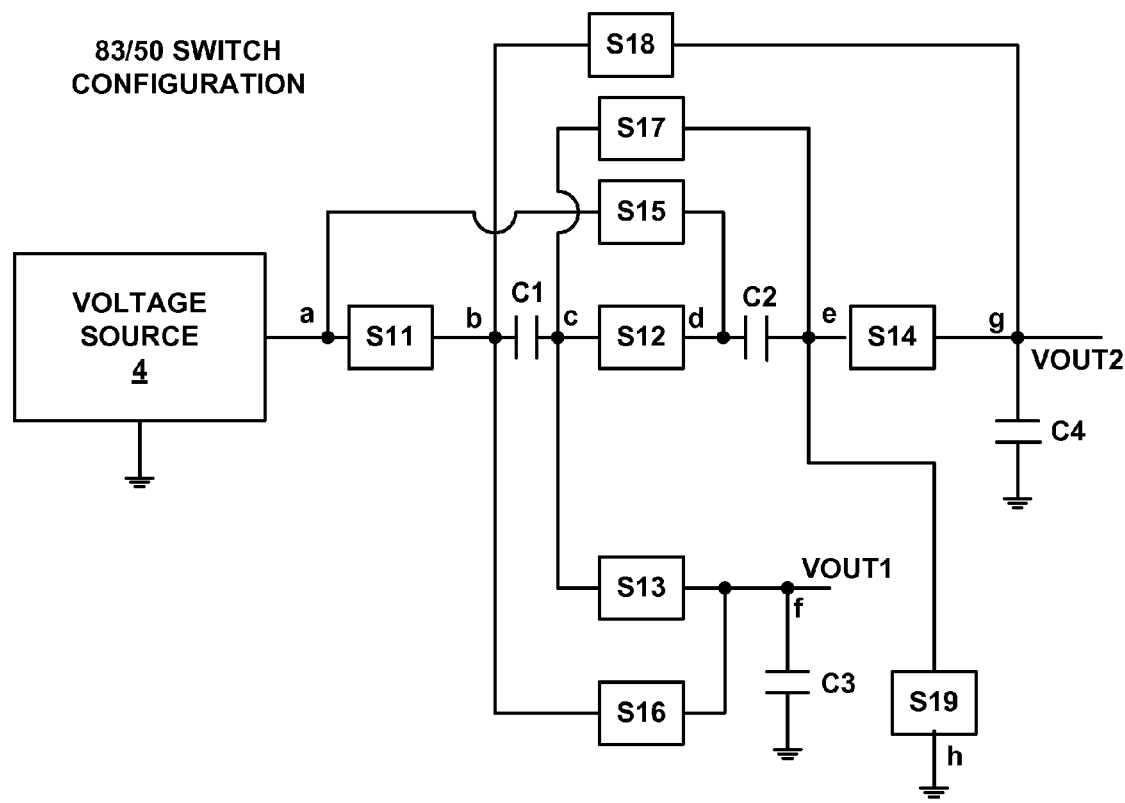
FIG. 5 is a circuit diagram illustrating a switch configuration for the dc-dc converter of FIG. 1 configured for an 83%/50% conversion ratio mode.

FIG. 5 is a circuit diagram illustrating a switch configuration for dc-dc converter 6 configured for an 83%/50% conversion ratio mode, i.e., a mode in which, approximately, VOUT1=0.83×VIN and VOUT2=0.5×VIN. In some implementations, dc-dc converter 6 includes switches S11-S19. In implementations in which dc-dc converter 6 is capable of providing the 80%/60% and 83%/50% modes (Table 1), dc-dc converter 6 may include both switches S1-S9 (FIG. 3) and switches S11-S19 (FIG. 5) in order to selectively support different conversion ratio modes. However, in each implementation, pump capacitors C1 and C2 and output capacitors C3 and C4 may be substantially the same.

As indicated in Table 1, for the first switch phase, nodes a and b are connected together, nodes c, d, and f are connected together, and nodes e and g are connected together. For the first switch phase, nodes a and b may be connected together by toggling ON switch S11. Nodes c, d, and f are connected together by toggling ON switches S12 and S13. Nodes e and g are connected together by toggling ON switch S14. Switches S15-S19 are left open such that no current can flow through them. Switches S11-S14 are the first set of switches that are toggled ON by switch controller 16 to transition to the first switch phase. Toggling ON only switches S11-S14 generates the subcircuit associated with the first switch phase for the 83%/50% conversion ratio mode.

For the second switch phase of the 83%/50% conversion ratio mode, nodes a and d are connected together, nodes e and f are connected together, and nodes c and e are connected together. For the second switch phase, nodes a and d are connected together by toggling ON switch S16. Nodes e and f are connected together by toggling ON switch S16. Nodes c and e are connected together by toggling ON switch S17. Switches S11-14 and switches S18-S19 are left open such that no current can flow through them. Switches S15-S17 are the second set of switches that are toggled ON by switch controller 16 to transition to the second switch phase. Toggling ON only switches S15-S17 generates the subcircuit associated with the second switch phase for the 83%/50% conversion ratio mode.

For the third switch phase of the 83%/50% conversion ratio mode, nodes b and g are connected together, nodes c and d are connected together, and nodes e and h are connected together. For the third switch phase, nodes b and g are connected together by toggling ON switch S18. Nodes c and d are connected together by toggling ON switch S12. Nodes e and h are connected together by toggling ON switch S19. Switches S11, S13-S17 are left open such that no current can flow through them. Switches S12 and S18-S19 are the third set of switches that are toggled ON by switch controller 16 to transition to the third switch phase. Toggling on only switches S12 and S18-S19 generates the subcircuit associated with the third switch phase for the 83%/50% conversion ratio mode. The subcircuit in the third switch phases is not coupled to input node a. In particular, neither capacitor C1 nor C2 is coupled to the input node, node a, in the subcircuit associated with the third switch phase.

FIGS. 3 and 5 describe switch configurations for two different dc-dc converter conversion ratio modes. As described above, in some implementations, switch matrix 7 only includes the switch configuration described with respect to FIG. 3. In some other embodiments, switch matrix 7 only includes the switch configuration described with respect to FIG. 5. In some other implementations, switch matrix 7 includes both of the switch configurations described with respect to FIGS. 3 and 5. In other implementations, switch matrix 7 includes switch configurations for one or more conversion ratio modes described in Table 1, including, in some cases, various combinations of such switch configurations. Various switch configurations can be designed to support the modes based on the connections of nodes a-h described in Table 1. For brevity and ease of description, however, only the switch configuration for the 80%/60% mode and the switch configuration for the 83%/50% mode are described with respect to FIGS. 3 and 5, respectively.

In embodiments where switch matrix 7 includes the switch configuration for the 80%/60% conversion mode and for the 83%/50% conversion mode, mode selection module 5 (FIG. 2) may transmit a signal to switch controller 16 to cause dc-dc converter 6 to switch from the 80%/60% conversion mode to the 83%/50% conversion mode or vice versa. In such embodiments, dc-dc converter 6 transitions from a three phase 80%/60% conversion mode to a three phase 83%/50% conversion mode, or vice versa. Similarly, in some embodiments, switch matrix 7 may include switches for only the 80%/60% conversion mode and the 67%/50% conversion mode. In such embodiments, mode selection module 5 may transmit a signal to switch controller 16 to cause dc-dc converter 6 to switch from the 80%/60% conversion mode to the 67%/50% conversion mode or vice versa. In such embodiments, dc-dc converter 6 transitions from a three phase 80%/60% conversion mode to a three phase 67%/50% conversion mode, or vice versa.

In yet another example embodiment, dc-dc converter 6 may include switches for the 80%/60% conversion mode, 67%/50% conversion mode, and 60%/40% conversion mode. In such embodiments, mode selection module 5 may transmit a signal to switch controller 16 to cause dc-dc converter 6 to switch from the 60%/40% conversion mode to the 67%/50% conversion mode. Then, at a later time, mode selection module 5 may transmit a signal to switch controller 16 to cause dc-dc converter 6 to switch from the 67%/50% conversion mode to the 80%/60% conversion mode. In such embodiments, dc-dc converter 6 transitions from a three-phase 60%/40% conversion mode, to a three-phase 67%/50% conversion mode, and then to a three phase 80%/60% conversion mode.

As described above, dc-dc converter 6 may transition from a three-phase conversion mode described in Table 1 to another three-phase conversion mode described in Table 1. Or, dc-dc converter 6 may transition from a three-phase conversion mode described in Table 1 to another three-phase conversion mode described in Table 1, and then to yet another three phase conversion mode described in Table 1. It may be possible to transition from any of the conversion modes described in Table 1 to any other conversion mode described in Table 1. The dc-dc converter 6 may transition between two of the conversion modes described in Table 1, three of the conversion modes described in Table 1, or more than three of the conversion modes described in Table 1.

FIGS. 6A-6C are circuit diagrams illustrating example subcircuits for the dc-dc converter 6 configured for the 80%/60% mode described above with reference to Table 1 and FIG. 3. FIG. 6A illustrates the subcircuit generated during the first switch phase. As shown in FIG. 6A, nodes a, b, and d are connected together, nodes c and f are connected together, and nodes e and g are connected together. Node h provides a common reference or ground potential for VIN, VOUT1, and VOUT2. In other words, switches S1-S4 (FIG. 3) are toggled ON, and switches S5-S10 (FIG. 3) are toggled OFF. Using basic circuit calculation techniques, it is apparent that, during the first switch phase, the first output voltage VOUT1 across output capacitor C3 is equal to the input voltage VIN minus the voltage drop across pump capacitor C1. The voltage drop across pump capacitor C1 will be referred to as voltage V1. The second output voltage VOUT2 across output capacitor C4 is equal to the input voltage VIN minus the voltage drop across pump capacitor C2. The voltage drop across capacitor C2 will be referred to as V2. Therefore, during the first switch phase, the following equations define the voltage levels at VOUT1 and VOUT2:

$$VOUT1 = VIN - V1$$

$$VOUT2 = VIN - V2$$

$$VOUT1 + V1 = VOUT2 + V2$$

FIG. 6B illustrates the subcircuit generated during the second switch phase. As shown in FIG. 6B, nodes a and d are connected together, nodes b and f are connected together, and nodes c, e, and g are connected together. Node h provides a common ground for VIN, VOUT1, and VOUT2. Otherwise stated, switches S4-S7 (FIG. 3) are toggled ON, and switches S1-S3 and S8-10 (FIG. 3) are toggled OFF. It is important to note that the polarity of capacitor C1 with respect to VOUT1 is inverted compared to the polarity of C1 in FIG. 6A. In particular, node c is coupled to VOUT1 at node f during the first switch phase, whereas, node b is coupled to VOUT1 at node f during the second switch phase. During the second switch phase, VOUT1 is equal to VIN minus V2 plus V1. The voltage across pump capacitor C1 is added due to the inversion of the polarity. VOUT2 is equal to VIN minus V2. Therefore, the following equations define the voltage level at VOUT1 and VOUT2 for the second switch phase:

$$VOUT1 = VIN - V2 + V1$$

$$VOUT2 = VIN - V2$$

$$VOUT1 + V2 - V1 = VIN$$

$$VOUT2 + V2 = VIN$$

$$VOUT1 - V1 = VOUT2$$

$$VOUT1 = VOUT2 + V1$$

FIG. 6C illustrates the subcircuit generated during the third switch phase. As shown in FIG. 6C, nodes b and g are connected together, nodes c and d are connected together, and nodes e and h are connected together. Node h provides a common reference or ground potential for VIN, VOUT1, and VOUT2. Otherwise stated, switches S8-S10 (FIG. 3) are toggled ON, and switches S1-S7 (FIG. 3) are toggled OFF. During the third switch phase, VOUT2 is equal to V1 plus V2. Neither capacitor C1 nor C2 is coupled to the input node, node a, in the subcircuit associated with the third switch phase. Therefore, the following equation defines the voltage at VOUT2 in the third switch phase of the 80%/60% conversion ratio mode:

$$VOUT2 = V1 + V2$$

In the third switch phase, as shown in FIG. 6C, the voltage VOUT1 is the voltage across output capacitor C3.

By using two equations from the first switch phase, the equation from the second switch phase, and the equation from the third switch phase, the voltage levels of VOUT1 and VOUT2 can be calculated as just a function of VIN. In particular, the subcircuits present at least four equations and four unknowns for calculation of output voltage values VOUT1 and VOUT2. The four equations are:

$$V2 + VOUT2 = VIN$$

$$VOUT1 + V1 = VOUT2 + V2$$

$$VOUT2 = V1 + V2$$

$$VOUT1 = VOUT2 + V1$$

The four equations can be rewritten to yield:

$$V2 + VOUT2 = VIN$$

$$V1 - V2 - VOUT2 + VOUT1 = 0$$

$$V1 + V2 - VOUT2 = 0$$

$$V1 + VOUT2 - VOUT1 = 0$$

Because this set of four equations include four unknowns (V1, V2, VOUT1, and VOUT2), VIN is known, all four become defined by applying basic algebra. For example, writing the four equations in matrix form yields:

$$\begin{bmatrix} 0 & 1 & 1 & 0 \\ 1 & -1 & -1 & 1 \\ 1 & 1 & -1 & 0 \\ 1 & 0 & 1 & -1 \end{bmatrix} \begin{bmatrix} V1 \\ V2 \\ VOUT2 \\ VOUT1 \end{bmatrix} = \begin{bmatrix} 1 \\ 0 \\ 0 \\ 0 \end{bmatrix} VIN$$

Subtracting the 3$^{rd}$ row from the 2$^{nd}$ row and 4$^{th}$ row yields:

$$\begin{bmatrix} 0 & 1 & 1 & 0 \\ 1 & -2 & 0 & 1 \\ 1 & 1 & -1 & 0 \\ 1 & -1 & 2 & -1 \end{bmatrix} \begin{bmatrix} V1 \\ V2 \\ VOUT2 \\ VOUT1 \end{bmatrix} = \begin{bmatrix} 1 \\ 0 \\ 0 \\ 0 \end{bmatrix} VIN$$

Multiplying the 1$^{st}$ row by two and adding it to the second row; subtracting the 1$^{st}$ row from the 3$^{rd}$ row; multiplying the 2$^{nd}$ row by 0.5 and subtracting it from the 4$^{th}$ row yields:

$$\begin{bmatrix} 0 & 1 & 1 & 0 \\ 1 & 0 & 2 & 1 \\ 1 & 1 & -2 & 0 \\ 0 & 0 & 2 & -1.5 \end{bmatrix} \begin{bmatrix} V1 \\ V2 \\ VOUT2 \\ VOUT1 \end{bmatrix} = \begin{bmatrix} 1 \\ 2 \\ -1 \\ 0 \end{bmatrix} VIN$$

Subtracting the 4$^{th}$ row from the 2$^{nd}$ row; multiplying the 2$^{nd}$ row by 1.5 and adding it to the 4$^{th}$ row yields:

$$\begin{bmatrix} 0 & 1 & 1 & 0 \\ 1 & 0 & 0 & 2.5 \\ 1 & 0 & -2 & 0 \\ 0 & 0 & 5 & 0 \end{bmatrix} \begin{bmatrix} V1 \\ V2 \\ VOUT2 \\ VOUT1 \end{bmatrix} = \begin{bmatrix} 1 \\ 2 \\ -1 \\ 3 \end{bmatrix} VIN$$

Multiplying the 4$^{th}$ row by 0.2 and subtracting it from the 1$^{st}$ row; multiplying the 4$^{th}$ row by 0.4 and adding it to the 3$^{rd}$ row; scaling the 2$^{nd}$ and 4$^{th}$ rows yields:

$$\begin{bmatrix} 0 & 1 & 0 & 0 \\ 1 & 0 & 0 & 1 \\ 1 & 0 & 0 & 0 \\ 0 & 0 & 1 & 0 \end{bmatrix} \begin{bmatrix} V1 \\ V2 \\ VOUT2 \\ VOUT1 \end{bmatrix} = \begin{bmatrix} 0.4 \\ 0.8 \\ 0.2 \\ 0.6 \end{bmatrix} VIN$$

Multiplying the matrix out yields the following solution to the four equations and four unknowns:

$V1=0.2*VIN$ $V2=0.4*VIN$ $VOUT1=0.8*VIN$ $VOUT2=0.6*VIN$

As can be seen by the equations, VOUT1 is 80% of VIN and VOUT2 is 60% of VIN. To summarize, FIGS. 6A-6C show subcircuits for the 80%/60% conversion ratio mode of dc-dc converter 6. In the 80%/60% mode, as indicated in Table 1, the conversion ratio at node f (FIG. 2) is 0.8, i.e., VOUT1/VIN=0.8, and the conversion ratio at node g (FIG. 2) is 0.6, i.e., VOUT2/VIN=0.6. FIG. 6A shows the subcircuit for the first switch phase, FIG. 6B shows the subcircuit for the second switch phase, and FIG. 6C shows the subcircuit for the third switch phase. Toggling selected switches ON or OFF to transition between the three subcircuits and associated switching phases, i.e., the first switch phase, the second switch phase, and the third switch phase, uniquely defines the voltage level values of VOUT1 and VOUT2, which are 0.8*VIN and 0.6*VIN, respectively.

The manner in which capacitors C1, C2, C3, and C4 are connected together in each subcircuit can be referred to as a subcircuit pattern of capacitors C1, C2, C3, and C4 for each subcircuit. Each subcircuit forms a different pattern of capacitors C1, C2, C3, and C4. Stated another way, in each subcircuit capacitors C1, C2, C3, and C4 are connected to one another in substantially different ways. For example, as shown in FIG. 6A, the combination of capacitors C2 and C4 are in parallel with the combination of capacitors C1 and C3. But, as shown in FIG. 6B, only capacitor C4 is in parallel with the combination of capacitors C1 and C3, and capacitor C2 is in series with the parallel combination of capacitors C1, C3, and C4. This is in contrast to capacitor pattern where all the capacitors are connected in substantially the same pattern. For example, if the capacitors are all connected in series with one another in each subcircuit, then each subcircuit would have the same pattern of capacitors. In accordance with this disclosure, each subcircuit has a different pattern of capacitors.

Notably, VOUT1 and VOUT2 are not dependent upon the values of capacitors C1, C2, C3, and C4. In general, capacitors C1, C2, C3, and C4 may be any value. In one embodiment, pump capacitors C1 and C2 each have a capacitance value equal to approximately 2.2 microfarads (uF), and output capacitors C3 and C4 each have a capacitance value equal to approximately 4.7 uF. Additionally, VOUT1 and VOUT2 are not dependent upon the frequency of the periodic wave generated by clock generator 14 (FIG. 2). In one embodiment, the frequency of the periodic wave generated by clock generator 14 may be approximately 8 kHz. Also, VOUT1 and VOUT2 are not dependent upon the order of the switching phases, i.e., the order of the first switch phase, second switch phase, and third switch phase if VOUT1 and VOUT2 are not loaded. For example, dc-dc converter 6 can transition from the first switch phase to the second switch phase, and then to the third switch phase. Or, dc-dc converter 6 can transition from the first switch phase to the third switch phase, and then to the second switch phase.

Also shown in FIGS. 6A-6C is the flow of charge within the subcircuits. Assume a charge y is transferred to VOUT1 in the second switch phase (FIG. 6B). Assume a charge z is transferred to VOUT2 in the third switch phase (FIG. 6C). This requires that in the first switch phase (FIG. 6A), capacitor C1 is charged by charges y+z from the input voltage VIN to compensate for the discharging in the other phases.

Because capacitor C2 is discharged by charge z in the third switch phase, capacitor C2 will be charged by charge z when it is connected between VIN and VOUT2 during the remainder of the switching cycle. So, assuming a charge x is transferred from VIN to capacitor C2 in the first switch phase, then a charge z-x must be transferred from VIN to capacitor C2 in the second switch phase, as a result the following equations are applicable:

$q$in$=x+y+z-x=y+2z$, in one switching cycle, where
  $q$in equals the charge from $VIN$ $q1=y+z+y=2y+z$, in one switching cycle, where $q1$
  equals the charge to $VOUT1$ $q2=x+z-x-y+z=2z-y$, in one switching cycle, where
  $q2$ equals the charge to $VOUT2$ Based on the three equations, qin can be solved as follows:

$q1=2y+z$ $2q1=4y+2z$ $q2=2z-y$ $2q1-q2=5y$ $q1+2q2=5z$ $q$in$=(2q1-q2)/5+2(q1+2q2)/5=4q1/5+3q2/5$, which
  equals $q$in$=0.8*q1+0.6*q2$ As can be seen by the preceding equations, the current conversion ratio from VOUT1 and VOUT2 to VIN is equal to the ideal voltage conversion ratio from VOUT1 and VOUT2 to VIN. Therefore, the energy of the system is preserved. This result is not dependent upon the actual input voltage, the values of capacitors C1-C4, the frequency of the periodic wave, or the order of the switching phases.

As described above, the conversion ratios of 0.8 and 0.6 are independent of the order of the switching phases, the frequency of the periodic wave, and the capacitor values. However, the output resistance at VOUT1 and VOUT2 is dependent upon the order of the switching phases, the frequency of the period wave, and the capacitor values for C1 and C2.

The output resistance at VOUT1 and VOUT2, when the order of the switching phase is the first switch phase, followed by the second switch phase, followed by the third switch phase, is calculated by applying an ideal voltage source of (0.8*VIN−V3) at VOUT1, applying an ideal voltage source of (0.6*VIN−V4) at VOUT2, and calculating the charge transfer at VOUT1 and VOUT2. V3 is the voltage drop at VOUT1 caused by a current IOUT1. Similarly, V4 is the voltage drop at VOUT2 caused by a current IOUT2. Assume the capacitance of C1 and C2 are equal, and sum to a variable CP, i.e., C1+C2=CP. Also assume that the switches are ideal, i.e., have zero impedance, the frequency of the periodic wave generated by clock generator 14 is f, and the capacitance value of C3 and C4 is substantially larger than the capacitance value of C1 and C2. Voltages V3 and V4 then can be calculated by the following equation:

$$V4=(14*IOUT2+9*4/3*IOUT1)/(25*CP*f)$$

$$V3=(8/3*3/4*IOUT2+16*IOUT1)/(25*CP*f)$$

The above equations show the effects of load regulation and cross load regulation. Load regulation is demonstrated by the output impedance at VOUT1 and VOUT2. The output impedance at VOUT1 is ROUT1 and the output impedance at VOUT2 is ROUT2. Cross load regulation is represented by the trans-impedance between VOUT1 and VOUT2. Based on the above equation, ROUT1 and ROUT2 are:

$$ROUT1=1/((25/16)*CP*f)$$

$$ROUT2=1/((25/14)*CP*f)$$

As can be seen from the previous equations, the values of ROUT1 and ROUT2 depend upon the values of capacitors C1 and C2 and the frequency of the periodic wave. Additionally, either IOUT1 or IOUT2 may be considered to have a scaling factor that is proportional to the ratio of the outputs, i.e., VOUT1/VOUT2 or VOUT2/VOUT1. From the view of IOUT1, IOUT2 has a scaling factor of 4/3. A scaling factor of 4/3 corresponds to VOUT1/VOUT2 where VOUT1 equal 0.8*VIN and VOUT2 equals 0.6*VIN, i.e., 0.8/0.6 equals 4/3. From the view of IOUT2, IOUT1 has a scaling factor of 3/4. A scaling factor of 3/4 corresponds to VOUT2/VOUT1, i.e., 0.6/0.8 which equals 3/4. The scaling factor is used to calculate the effective ROUT1 and ROUT2 as described below.

The ratio of ROUT2/ROUT1 equals 7/8. Taking into account the scaling factor, the ratio can be rewritten as (4/3)*ROUT2/ROUT1=7/6. The scaled value, i.e., (4/3)*ROUT2, can be considered as an effective output resistance to be compared to ROUT1. Thus, the effective output resistance at VOUT2 is approximately 17% larger than ROUT1. Therefore, it is beneficial to connect digital circuitry to VOUT2 and analog circuitry to VOUT1. Even though ROUT1 is 14% larger than ROUT2, this result may not be undesirable. Generally, a lower output resistance is preferred.

In addition to providing output resistance, the output voltages may have an effect on one another. VOUT1 may affect VOUT2. Similarly, VOUT2 may affect VOUT1. Cross load regulation is the term used to describe the effects of one of the output voltages on the other. The amount of cross load regulation rejected by VOUT2, i.e., the amount that VOUT2 rejects the effects of VOUT1 can be calculated. For example, the ratio of load regulation and effective cross load regulation seen at VOUT1 is equal to:

$$(3/4)*(\partial V3/\partial IOUT1)/(\partial V3/\partial IOUT2)=6$$

In the equation above, ∂ indicates a change in the pertinent value. From the equation above, the voltage variation of VOUT1 due to IOUT2 effectively is a factor of 6 smaller compared to the voltage variation of VOUT1 due to IOUT1. The ratio of load regulation and effective cross-load regulation seen at VOUT2 is equal to:

$$(4/3)*(\partial V4/\partial IOUT2)/(\partial V4/\partial IOUT1)=14/9=1.6$$

This means that the voltage variation of VOUT2 due to IOUT1 effectively is a factor of 1.6 smaller compared to the voltage variation of VOUT2 due to IOUT2. Thus, VOUT1 is 6/1.6=3.9 times less sensitive for VOUT2 than vice versa. Consequently, VOUT1 may be more suited to supply analog circuits than VOUT2.

As described earlier, dc-dc converter 6 can transition from the first switch phase to the second switch phase, then to the third switch phase, and back to the first switch phase. Or, alternatively, dc-dc converter 6 can transition from the first switch phase to the third switch phase, then to the second switch phase, and back to the first switch phase. However, as stated earlier, in the case where dc-dc converter 6 transitions from the first switch phase to the third switch phase, then to the second switch phase, and back to the first switch phase, the dc-dc converter circuit may yield less favorable second order effects.

The output resistance for this transition path (first switch phase to third switch phase to second switch phase) can be calculated in a substantially similar manner as that above. For this example, the equations for V3 and V4 are:

$$V4=(14*IOUT2+2*IOUT1)/(25*CP*f)$$

$$V3=(12*IOUT2+16*IOUT1)/(25*CP*f)$$

The equation for V3 can be rewritten to yield:

$$V3=((16)*(3/4)*IOUT2+16*IOUT1)/(25*CP*f)$$

In this case, VOUT2 is highly independent from VOUT1. However, VOUT1 provides no rejection from VOUT2, which may cause VOUT1 to fluctuate in voltage based on the output at VOUT2. Because VOUT1 may be coupled to analog devices that are more susceptible to voltage variation, this implementation (first switch phase to third switch phase to second switch phase) may provide less favorable second order effects compared to the implementation where dc-dc converter 6 transitions from the first switch phase to the second switch phase, then to the third switch phase, and back to the first switch phase.

To summarize, for the 80%/60% conversion mode, when dc-dc converter 6 transitions from the first switch phase, shown in FIG. 6A, to the second switch phase, shown in FIG. 6B, and then to the third switch phase, shown in FIG. 6C, VOUT1 equals 0.8*VIN and VOUT2 equals 0.6*VIN. Additionally, VOUT1 is highly independent of VOUT2 such that it may be desirable to couple VOUT1 to analog devices within electrical system 2. In this case, VOUT2 is partially dependent on VOUT1, however, such that it may be desirable to coupled VOUT2 to digital devices within electrical system 2.

Figure 7A:
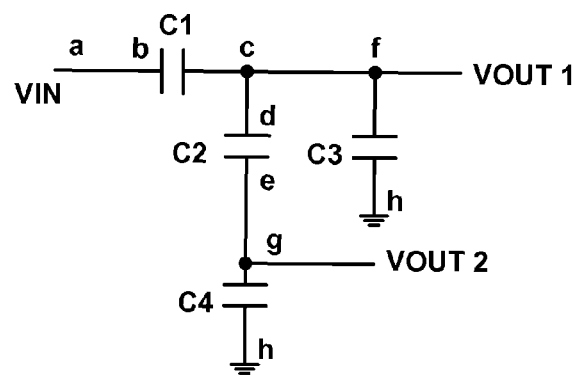
FIGS. 7A-7C are circuit diagrams illustrating subcircuits for the dc-dc converter configured for the 83%/50% conversion ratio mode.
Figure 7B:
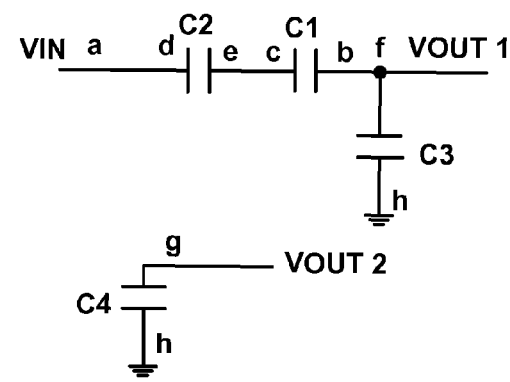
Figure 7C:
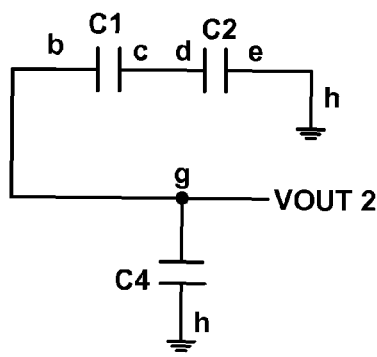

FIGS. 7A-7C are circuit diagrams illustrating subcircuits for the dc-dc converter 6 configured for a 83%/50% conversion ratio mode. FIG. 7A is the subcircuit generated during the first switch phase of the 83%/50% conversion ratio mode. As shown in FIG. 7A, nodes a and b are connected together, nodes c, d, and f are connected together, and nodes e and g are connected together. Node h provides a common ground for VIN, VOUT1, and VOUT2. Otherwise stated, switches S11-S14 (FIG. 5) are toggled ON, and switches S15-S19 (FIG. 5)

are toggled OFF. Using basic circuit calculation techniques, it is apparent that during the first switch phase:

$$VOUT1=VIN-V1$$

$$VOUT2=VIN-V1-V2$$

$$VOUT1=VOUT2+V2$$

FIG. 7B is the subcircuit generated during the second switch phase of the 83%/50% conversion ratio mode. As shown in FIG. 7B, nodes a and d are connected together, nodes e and f are connected together, and nodes c and e are connected together. Node h provides a common ground for VIN, VOUT1, and VOUT2. Otherwise stated, switches S15-S17 (FIG. 5) are toggled ON, and switches S11-S4 and S18-19 (FIG. 5) are toggled OFF. It is important to note that the polarity of capacitor C1 is inverted compared to the polarity of C1 in FIG. 7A. During the second switch phase of the 83%/50% conversion ratio mode:

$$VOUT1=VIN-V2+V1$$

FIG. 7C is the subcircuit generated during the third switch phase of the 83%/50% conversion ratio mode. As shown in FIG. 7C, nodes b and g are connected together, nodes c and d are connected together, and nodes e and h are connected together. Node h provides a common ground for VIN, VOUT1, and VOUT2. Otherwise stated, switches S12 and S18-S19 (FIG. 5) are toggled ON, and switches S11 and S13-S17 (FIG. 5) are toggled OFF. Neither capacitor C1 nor C2 is coupled to the input node, node a, in the subcircuit associated with the third switch phase. During the third switch phase of the 83%/50% conversion ratio mode:

$$VOUT2=V1+V2$$

Similar to FIGS. 6A-6C, the voltage equations for each phase of the 83%/50% conversion ratio mode yield four independent equations with four unknowns (VOUT1, VOUT2, V1, and V2), VIN is known. The four equations are:

$$VOUT1+V1=VIN$$

$$VOUT1-VOUT2-V2=0$$

$$VOUT1-V1+V2=VIN$$

$$VOUT2-V1-V2=0$$

Substantially the same steps described with respect to FIGS. 6A-6C can be applied to calculate the value of each unknown in the above equations for the 83%/50% conversion ratio mode. By using basic algebra to solve the equations, VOUT1 equals 5/6*VIN and VOUT2 equals 1/2*VIN. VOUT1 written in decimal form substantially equals 0.83*VIN. VOUT2 written in decimal form equals 0.5*VIN.

To summarize, FIGS. 7A-7C show subcircuits for the 83%/50% mode. In the 83%/50% mode, as indicated in Table 1, the conversion ratio at node f (FIG. 2) is approximately 0.83, i.e., VOUT1/VIN=0.83, and the conversion ratio for a node g (FIG. 2) is 0.5, i.e., VOUT2/VIN=0.5, at no load. FIG. 7A shows the subcircuit for the first switch phase, FIG. 7B shows the subcircuit for the second switch phase, and FIG. 7C shows the subcircuit for the third switch phase. Toggling switches to transition between the three switching phases, i.e., the first switch phase, the second switch phase, and the third switch phase, uniquely defines VOUT1 and VOUT2, which are 0.83*VIN and 0.5*VIN, respectively. Similar to FIGS. 6A-6C, as shown in FIGS. 7A-7C, each subcircuit has a different pattern of capacitors.

Switch configurations and subcircuits have been shown for two conversion modes. FIGS. 3 and 6A-6C show switch configuration and subcircuits for the 80%/60% mode. FIGS. 5 and 7A-7C show switch configuration and subcircuits for the 83%/60% mode. As described above, switch configurations can be readily implemented for other conversion ratio modes described in Table 1 in view of this disclosure, and particularly in view of the switch configurations illustrated in FIGS. 3 and 5. Similarly, subcircuits can be readily implemented for other conversion ratio modes described in Table 1 in view of this disclosure, and particularly in view of the subcircuits shown in FIGS. 6A-6C and 7A-7C. For each conversion ratio mode described in Table 1, the pattern of capacitors for each subcircuit is different.

In the examples described above, dc-dc converter 6 comprises three subcircuits for every conversion ratio, i.e., a first switch phase subcircuit, a second switch phase subcircuit, and a third switch phase subcircuit. Switch controller 16 transmits a signal to dc-dc converter 6 to toggle a plurality of switches to transition between the three phases. Again, the transitions may be arranged in different patterns or sequences. As one example, however, the dc-dc converter 6 may transition from the first switch phase to the second switch phase, then to the third switch phase and back to the first switch phase based on the desired conversion ratio. In this example, dc-dc converter 6 may be configured to produce a variety of different conversion rations, but only requires two capacitors. The use of three phases with two capacitors may support the realization of a variety of different conversion ratios.

In some aspects, however, the disclosure further contemplates a dc-dc converter that provides a conversion mode that requires two capacitors and only two switching phases to generate a conversion ratio such that VOUT1 equals 0.75*VIN and VOUT2 equals 0.5*VIN in addition to one or more conversion modes described in Table 1. In this implementation, a dc-dc converter and associated components in an electrical system may be configured to support selective operation in different modes, such as a two capacitor/three phase mode (e.g., with an 80%/60% conversion ratio) or a two-capacitor/two phase mode (e.g., with a 75%/50% conversion ratio).

Figure 8:
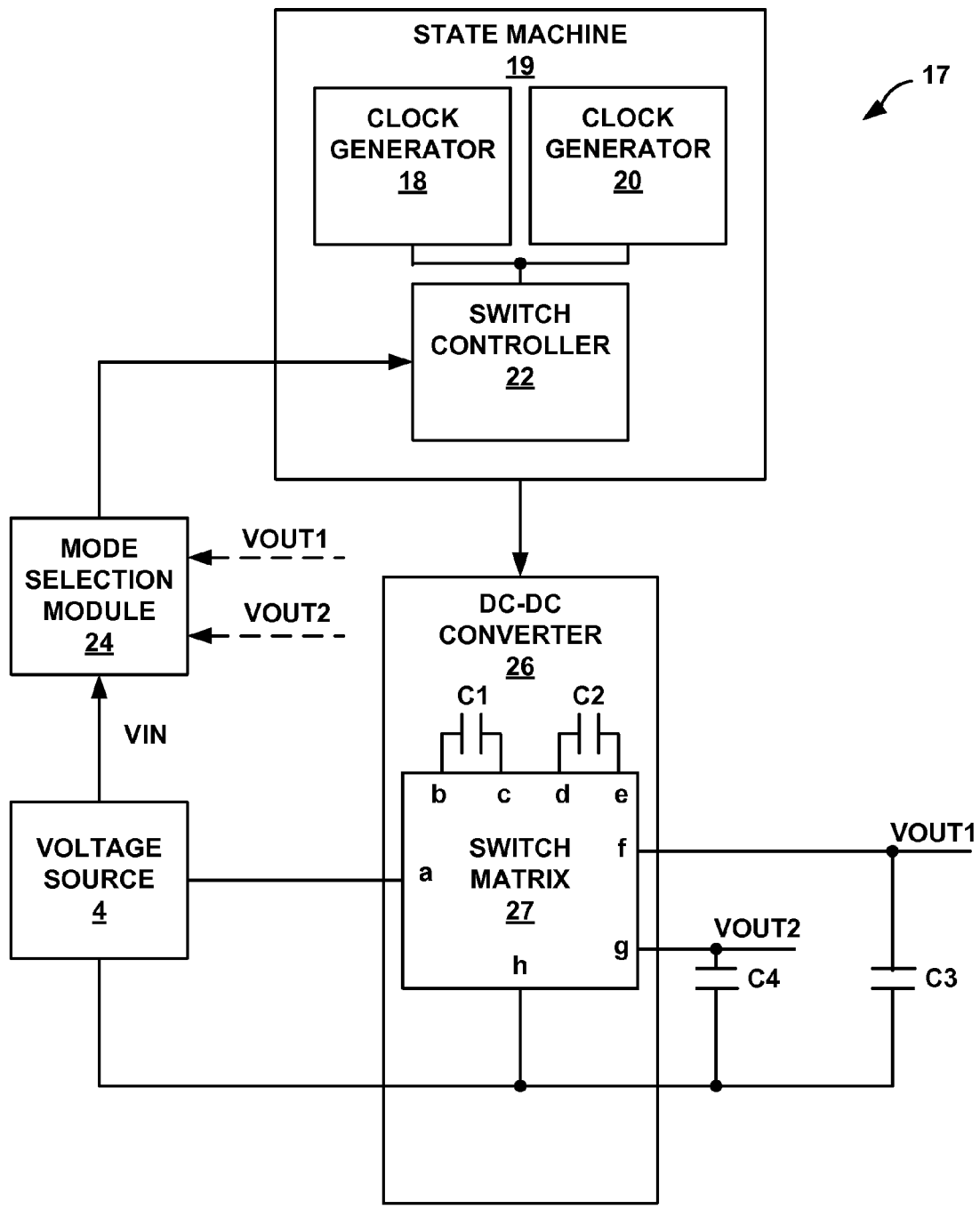
FIG. 8 is a block diagram illustrating an electrical system that includes two clock sources.

FIG. 8 is a block diagram illustrating an electrical system 17 in accordance with another example implementation. In the example of FIG. 8, system 17 may include clock generator 18 and clock generator 20, although a single clock generator may be used in some implementations. As shown in FIG. 8, electrical system 17 includes dc-dc converter 26. The dc-dc converter 26 may be substantially similar to dc-dc converter 6. For example, dc-dc converter 26 may provide some or all of the conversion ratios described in Table 1. The dc-dc converter 26 includes switch matrix 27. Switch matrix 27 may be substantially similar to switch matrix 7. For example, switch matrix 27 may include a plurality of switches that are toggled ON and OFF on a selective basis to transition dc-dc converter 26 through three phases, as described above with reference to switch matrix 7.

In addition to providing one, some or all of the conversion ratios described in Table 1, in the example of FIG. 8, dc-dc converter 26 also may be configured to provide a 75%/50% and/or a 50%/25% conversion mode. In the 75%/50% conversion mode, the conversion ratio VOUT1/VIN equals 0.75 and the conversion ratio VOUT2/VIN equals 0.5. Similarly, in the 50%/25% conversion mode, the conversion ratio VOUT1/VIN equals 0.5 and the conversion ratio VOUT2/VIN equals 0.25.

Both the 75%/50% conversion mode and the 50%/25% conversion mode make use of two capacitors (C1 and C2) and two switching phases (charge and pump), in contrast to the modes contemplated by Table 1, which use two capacitors and three switching phases (first switch phase, second switch phase, and third switch phase). Table 2 defines an example of the interconnection between nodes a-h for the two switching phases, as well as, interconnection between nodes a-h, to generate conversion ratios of 0.75/0.5 and 0.5/0.25.

TABLE 2

| dc-dc conversion mode | Nodes that are interconnected within switch matrix 27 | | Conversion Ratio VOUT1/VIN | Conversion Ratio VOUT2/VIN |
| --- | --- | --- | --- | --- |
| | Charge Phase | Pump Phase | | |
| 75%/50% | abd, cf, eg | bf, cdg, eh | 0.75 | 0.5 |
| 75%/50% | ab, cf, dg, eh | ad, bf, ceg | 0.75 | 0.5 |
| 50%/25% | ad, bef, cg | bg, ceh, df | 0.5 | 0.25 |
| 50%/25% | ad, bg, ch, ef | bdf, cg, eh | 0.5 | 0.25 |

As indicated by Table 2, there are two different switch configurations for the 75%/50% mode and 50%/25% mode. Switch matrix 27 may provide switches for only one of the 75%/50% modes and 50%/25% modes. However, the other modes are provided as further examples for purposes of illustration. In some embodiments, switch matrix 27 may only include switches for one of the 75%/50% modes in Table 2 and switches for one or more conversion modes described in Table 1. Similarly, in some other embodiments, switch matrix 27 may only include switches for one of the 50%/25% modes in Table 2 and switches for one or more conversion modes described in Table 1.

As shown in FIG. 8, electrical system 17 includes state machine 19. State machine 19 may be substantially similar to state machine 8 (FIGS. 1 and 2). In the example of FIG. 8, however, state machine 19 includes two different clock generators. Clock generator 18 outputs a periodic wave and may be substantially similar to clock generator 14 (FIG. 2). Clock generator 20 outputs a periodic wave, but the frequency of the periodic wave may be different than the frequency of the periodic wave generated by clock generator 18. In some implementations, the frequency of the periodic wave generated by clock generator 20 may be faster than the frequency of the periodic wave generated by clock generator 18. For example, the frequency of clock generator 20 may be approximately 33% faster than the frequency of clock generator 18.

The use of a faster frequency for clock generator 20 may be desirable in order to maintain a desirable output impedance when dc-dc converter 26 operates in a two-phase, conversion ratio mode. More specifically, a clock generator 20 with a faster frequency may be used to drive switch controller 22 when dc-dc converter 26 operates in a mode that makes use of two pump capacitors and two phases. A clock generator 18 with a slower frequency may be used to drive switch controller 22 when dc-dc converter 26 operates in a mode that makes use of two pump capacitors and three phases. As an example, if clock generator 18 generates a waveform at a frequency of approximately 8 kHz, then clock generator 20 may generate a waveform at a frequency of approximately 8 kHz× 1.33=10.67 kHz.

In other implementations, a single clock generator may be used for both two-phase and three-phase modes of dc-dc converter 26, rather than two clock generators. However, the use of a slower clock generators 18 and a faster clock generator 20 for three-phase and two-phase modes, respectively, may be desirable in order to maintain a desirable output impedance in the two-phase mode, as discussed above. Accordingly, the disclosure should not be limited to the use of two clock generators for the example of FIG. 8, although the use of two clock generators may be desirable. Moreover, in various implementations, clock generators 18, 20 may be formed from different clocks, or a single clock with suitable frequency multiplier or divider circuitry to produce desired clock frequencies.

As described above, in some embodiments, clock generator 20 may not be necessary. In such embodiments, switch controller 22 is only clocked out by the periodic wave generated by clock generator 18. As described above, dc-dc converter 26 transitions from the charge phase to the pump phase every rising or falling edge of the periodic wave. However, for the 75%/50% conversion mode, in embodiments that do not require clock generator 20, dc-dc converter 26 may transition from the charge phase to the pump phase after the occurrence of two consecutive rising or falling edges of the periodic wave generated by clock generator 18. Similarly, dc-dc converter 26 may transition from the pump phase to the charge phase after the occurrence of two consecutive rising or falling edges. In such embodiments, in the 75%/50% conversion mode, switch controller 22 may be programmed to transmit a signal to dc-dc converter 26 after two consecutive rising or falling edges, then transmit a signal to dc-dc converter 26 after only one rising or falling edge, and repeating the steps for the 75%/50% conversion mode. For any of the three-phase conversion modes described in Table 1, dc-dc converter 26 transitions from one phase to another on every rising or falling edge of the periodic wave.

As one example, assuming an 8 kHz periodic wave, the amount of time that dc-dc converter 26 remains in a switching phase for any of the conversion modes described in Table 1 is 125 microseconds (us), ⅛ kHz=125 us. Therefore, the total cycle time for any of the conversion modes described in Table 1 is 375 us, i.e., 125 us for each of the three phases. In embodiments where clock generator 20 is not necessary, as described above, for the 75%/50% converter mode, dc-dc converter 26 transitions from the charge phase to the pump phase or vice versa every two consecutive rising or falling edges of the periodic wave. Assume that the transition from the charge phase to the pump phase requires two consecutive rising edges. Therefore, the amount of time that dc-dc converter 26 remains in the charge phase for the 75%/50% conversion mode is 250 us (⅛ kHz*2). The amount of time that dc-dc converter 26 remains in the pump phase for the 75%/50% converter mode is 125 us. In such embodiments, the total cycle time for the 75%/50% is 375 us (250 us+125 us), which is the same as the total cycle time for the conversion modes described in Table 1. Similarly, if the transition from the pump phase to the charge phase required two consecutive rising edges, then the amount of time that dc-dc converter 26 remains in the pump phase is 250 us, and the amount of time that dc-dc converter 26 remains in the charge phase is 125 us. Once again, the total cycle time will be 375 us which is the same as the total cycle time for the conversion modes described in Table 1.

State machine 19 also includes switch controller 22. Switch controller 22 may be substantially similar to switch controller 16. However, switch controller 22 can also provide a signal to toggle the switches for the 75%/50% and 50%/25% conversion modes. Hence, switch controller 22 may be programmed or otherwise configured to control switch matrix 27 to support one or more of conversion ratio modes set forth in Table 1 and one or more of the conversion ratio modes set forth in Table 2 on a selective basis. In this manner, dc-dc converter 26 may use two pump capacitors and three phases in one mode (e.g., 80%/60%) and two pump capacitors and two phases in another mode (e.g., 75%/50%). Switch controller 22 may provide the signal to toggle the switches for the additional 75%/50% or 50%/25% conversion modes using techniques similar to those described above with respect to switch controller 16.

Stated another way, dc-dc converter 26 includes an input node (node a) that receives a dc input voltage from voltage source 4 at an input level. Either node f, node g, or both node f and g provide output levels. Dc-dc converter 26 includes a plurality of switches within switch matrix 27. The switches within switch matrix 27 are configured to selectively arrange capacitors C1 and C2 in different subcircuits. Switch controller 22 is configured to control the switches within switch matrix 27 to transition between a first number of phases, i.e., three phases for the conversion modes described in Table 1, comprising a first set of subcircuits in a first conversion mode, i.e., the subcircuits for the first phase, second phase, and third phase for the 80%/60% conversion mode.

Switch controller 22 transitions between a first number of phases and between a second number of phases, i.e., two phases for the conversion modes described in Table 2, comprising a second set of subcircuits in a second conversion mode, i.e., the subcircuits for the charge phase and pump phase for the first 75%/50% conversion mode. In this manner, the first number of phases is different than the second number of phases. As one example, the first number of phases may be three and the second number of phases may be two that correspond to the conversion modes in Table 1 and Table 2, respectively. The phases for a mode or modes may differ in length. Different durations of the phases may allow for an implementation in which a two-phase converter is driven by a clock that was designed for a three-phase mode. For example, by choosing one of the two phases in the two-phase mode to be equal to the sum of two of the three phases in the three-phase mode, the two-phase mode may have one phase that last twice as long as the other phase.

The output level at either node f or node g will be different in the first conversion mode and the second conversion mode. For example, the output level at node f will be 80% of VIN and the output level at node g will be 60% of VIN for the 80%/60% three phase conversion mode. The output level at node f will be 75% of VIN and the output level at node g will be 50% of VIN for the 75%/50% two phase conversion mode.

In implementations in which switch controller 22 provides a signal to toggle the switches for one of the conversion modes described in Table 1, clock generator 18 provides the periodic wave that clocks the signal out of switch controller 22. The conversion modes described in Table 1 may be considered a first conversion mode. In embodiments, where switch controller 22 is providing a signal to toggle the switches for one of the conversion modes described in Table 2, clock generator 20 provides the periodic wave that clocks the signal out of switch controller 22. The conversion modes described in Table 2 may be considered a second conversion mode. Hence, either clock generator 18 or clock generator 20 may be used by switch controller 22 according to the particular conversion mode that is selected for dc-dc converter 26. In a two-phase mode as contemplated by Table 2, clock generator 20 may be used to provide a slightly higher clock frequency (e.g., 33 percent higher than frequency of clock generator 18) in order to maintain a desirable output impedance of dc-dc converter 26, as described above.

As can be ascertained from Table 2, in the conversion modes described in Table 2, a ratio x for the first output level to the input level, i.e., VOUT1/VIN, and a ratio for the second output level to the input level, i.e., VOUT2/VIN, represented as a percentage value, is one of x/y equal to approximately 75%/50% or 50%/25%.

As shown in FIG. 8, electrical system 17 may include mode selection module 24. In some cases, mode selection module 24 may be coupled to voltage source 4 as well as state machine 19. In some cases, mode selection module 24 may select either a conversion mode described in Table 1 or a conversion mode described in Table 2 based on the input level of voltage source 4. Mode selection module 24 may include a comparator that compares the voltage of voltage source 4 to a threshold voltage level. When the voltage of voltage source 4 is greater than the threshold voltage level, mode selection module 24 may output a signal to state machine 19 indicating that switch controller 22 should toggle the switches for one of the 75%/50% modes, i.e., using two pump capacitors and two phases. In such situations, the output of switch controller 22 is clocked out by clock generator 20.

When the voltage of voltage source 4 is less than the threshold voltage level, however, mode selection 24 may output a signal to state machine 19 indicating that switch controller 22 should toggle the switches for the 80%/60% mode, i.e., using two pump capacitors and three phases. In such situations, the output of switch controller is clocked out by clock generator 18. Mode selection module 24 may output its signal using techniques similar to those described with respect to mode selection module 5.

As an illustration, if voltage source 4 comprises a battery having a nominal voltage of 3.3 volts (V), mode selection module 24 may select a threshold voltage value of 2.5 volts. When a comparator associated with mode selection module 24 determines that the input voltage level from voltage source 4 has dropped below 2.5 volts due to battery charge depletion, mode selection module 24 may control switch controller 22 to implement an 80%/60% conversion ratio using two pump capacitors and three phases, instead of a 75%/60% conversion ratio using two pump capacitors and two phases. In this manner, dc-dc converter 26 transitions from a three-phase conversion mode to a two-phase conversion mode.

In some embodiments, mode selection module 24 may include a plurality of comparators. Each one of the plurality of comparators may compare the voltage from voltage source 4 with a respective threshold voltage level. The threshold voltage level for each comparator may be different. As an example, if the voltage from voltage source 4 is 3.3 V, mode selection module 24 may include two comparators. Different implementations may have more than two comparators. The threshold voltage level for the first comparator may be 3.2 V. The threshold voltage level for the second comparator may be 2.5V.

In this example, mode selection module 24 may be configured to select the 60%/40% conversion mode while the voltage from voltage source 4 is greater than 3.2V. In this case, the first and second comparators indicate the input voltage level is above 3.2 V and above 2.5 V, respectively. Mode selection module 24 may transmit a signal to state machine 19 that indicates that the selected mode is 60%/40%. In response, switch controller 22 transmits a signal to switch matrix 27 that defines which switches need to be toggled ON and OFF and in which order based on Table 1. For the 60%/40% mode, the output signal of switch controller 22 may be clocked out by clock generator 18.

In response to the outputs of the first and second comparators, mode selection module 24 may select the 75%/50% conversion mode while the voltage from voltage source 4 is less than 3.2 V and greater than 2.5 V. In this case, the first and second comparators indicate the input voltage level is below 3.2 V but above 2.4V, respectively. Mode selection module 24 transmits a signal to state machine 19 that indicates that the selected mode is 75%/50%. In response, switch controller 22 transmits a signal to switch matrix 27 that defines which switches need to be toggled ON and OFF and in which order based on Table 2. For the 75%/50% mode, the output signal of switch controller 22 is clocked out by clock generator 20.

Mode selection module 24, in this example, selects the 80%/60% conversion mode when the voltage from voltage source 4 is less than 2.5V. Mode selection module 24 transmits a signal to state machine 19 that defines that the selected mode is 80%/60%. In response, switch controller 22 transmits a signal to switch matrix 27 that defines which switches need to be toggled and in which order based on Table 1. For the 80%/60% mode, the output signal of switch controller 22 is clocked out by clock generator 20.

In the above example, mode selection module 24 controls switch controller 22 and switch controller 22, in turn, controls switch matrix 27, to selectively toggle switches in the switch matrix so that dc-dc converter 26 uses a 60%/40% conversion ratio mode (with two pump capacitors and three phases (first, second and third) per Table 1) when the input voltage level is at or above 3.2 V, a 75%/50% conversion ratio mode when the input voltage level is at or above 2.5 V but below 3.2 V (with two pump capacitors and two phases (charge and pump) per Table 2), and an 80%/60% conversion ratio mode when the input voltage level is below 2.5 V (with two pump capacitors and three phases per Table 1). In this manner, dc-dc converter 26 transitions from a three-phase conversion mode (60%/40%) to a two-phase conversion mode (75%/50%), and then to a three phase conversion mode (80%/60%). In some embodiments, dc-dc converter 26 may transition from a three-phase conversion mode to another three-phase conversion mode based on the threshold voltage level. In some other embodiments, dc-dc converter 26 may transition from a three-phase conversion mode to another three-phase conversion mode followed by yet another three-phase conversion mode.

As described above and shown in FIG. 8, mode selection module 24 measures the input voltage to determine whether to switch conversion modes. In some embodiments, mode selection module 24 may alternatively or additionally measure the output voltage of either VOUT1 or VOUT2, or both. In such embodiments, mode selection module 24 transmits a signal to state machine 19 to switch conversion modes when the voltage at one or both VOUT1 or VOUT2 drops below a predetermined, respective threshold value in accordance with techniques substantially similar to those described above. For example, if VOUT1 or VOUT2 becomes too low, relative to a respective threshold, then the mode may be changed to provide higher conversion ratios. If VIN is sufficiently high, then the mode may be changed to a lower conversion ratio. In FIG. 8, mode selection module 24 is shown as optionally receiving VOUT1 and/or VOUT2, as indicated by the dashed line inputs. If VOUT1 drops below a first applicable threshold, mode selection module 24 may select a higher conversion ratio mode of the dc-dc converter. Similarly, if VOUT2 drops below a second applicable threshold, which may be different from the first applicable threshold, mode selection module 24 may select a higher conversion ratio mode of the dc-dc converter. Selection of a different conversion ratio mode may be determined based on comparison of VOUT1 to the first threshold, VOUT2 to the second threshold, or comparison of both to the respective thresholds. However, comparison of VOUT1 and VOUT2 is optional, and may be an alternative or additional determination relative to comparison of VIN to an applicable threshold. In typical implementations, mode selection module 24 may rely on the comparison of VIN to an applicable threshold or thresholds.

Hence, in the example of FIG. 8, dc-dc converter 26 is controlled to transition between modes having two pump capacitors and three phases and modes having two pump capacitors and two phases. In this manner, system 17 can provide a variety of different conversion modes to support reliable output voltage levels across a range of input voltage levels. The ability to transition between two, three or more conversion ratio modes, taking advantage of two-phase and three-phase modes in some implementations, can provide additional levels of conversion ratio gradation to support a wide range of input voltage levels.

Figure 9:
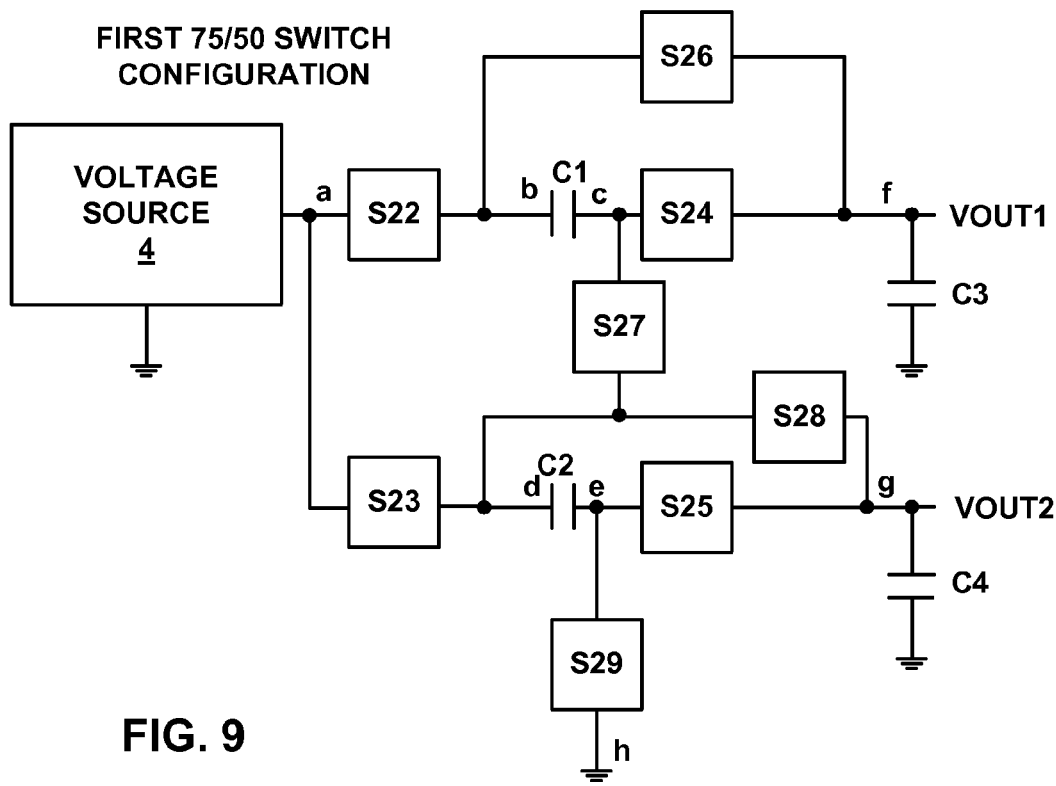
FIG. 9 is a circuit diagram illustrating a first switch configuration for the dc-dc converter of FIG. 1 configured for the 75%/50% conversion ratio mode.

FIG. 9 is a circuit diagram illustrating a first switch configuration for the dc-dc converter configured for the 75%/50% mode. As indicated in the second row of Table 2, for the charge phase, nodes a, b, and d are connected together, nodes c and f are connected together, and nodes e and g are connected together. For the charge phase, nodes a, b, and d are connected together by toggling ON switches S22 and S23. Nodes c and f are connected together by toggling ON switch S24, and nodes e and g are connected together by toggling ON switch S25. Switches S26-S29 are left open or toggled OFF such that no current can flow through them. Switches S22-S25 are the first set of switches that are toggled ON by switch controller 22 to transition to the charge phase. Toggling ON only switches S22-S25 generates the subcircuit associated with the charge phase for the first 75%/50% mode.

For the pump phase, nodes b and f are connected together, nodes c, d, and g are connected together, and nodes e and h are connected together. For the pump phase, nodes b and f are connected together by toggling ON switch S26. Nodes c, d, and g are connected together by toggling ON switches S27 and S28. Nodes e and h are connected together by toggling ON switch S29. All other switches are left open or, in effect, toggled OFF. Switches S26-S29 are the second set of switches that are toggled ON by switch controller 22 to transition to the pump phase from the charge phase. Toggling ON only switches S26-S29 generates the subcircuit associated with the pump phase for the first 75%/50% mode.

The first switch phase for the 80%/60% conversion mode and the charge phase for the first 75%/50% conversion mode may require the same nodes of switch matrix 27 to be connected together. As described in Table 1, for the 80%/60% conversion mode, nodes a, b, and d are connected together, nodes c and f are connected together, and nodes e and g are connected together. Similarly, as described in Table 2, for the first 75%/50% conversion mode, nodes a, b, and d are connected together, nodes c and f are connected together, and nodes e and g are connected together. Appropriate switches within switch matrix 27 may be selectively toggled on to realize such interconnections. In embodiments where dc-dc converter 26 is configured to provide both the 80%/60% conversion mode and the first 75%/50% conversion mode, switch matrix 27 may use the same switches for the first phase for both the 80%/60% conversion mode and the first 75%/50% conversion mode. Stated another way, in some implementations, switches S1-S4 (FIG. 3) may be the same switches as S22-S25 (FIG. 9).

In embodiments where dc-dc converter 26 transitions from the 80%/60% (three phase) mode to the 75%/50% (two-phase) mode, or vice versa, the voltages across capacitors C1 and C2 are adapted to the change in conversion ratio. As described above, the voltage across C1 in the 80%/60% conversion mode is 0.2*VIN. In the first 75%/50% conversion mode, the voltage across C1 is 0.25*VIN. The voltage across C2 in the 80%/60% conversion mode is 0.4*VIN. The voltage across C2 in the first 75%/50% conversion mode is 0.5*VIN. Since the difference in the voltage across C1 in the 80%/60% conversion mode and the voltage cross C1 in the first 75%/50% conversion mode is rather small, i.e., the difference between 0.25*VIN and 0.2*VIN is rather small, changing conversion modes from the 80%/60% mode to the first 75%/50% mode ordinarily will not result in much wasted energy. Similarly, since the difference in the voltage across C2 in the 80%/60% conversion mode and the voltage across C2 in the first 75%/50% conversion mode is also rather small, i.e., the difference between 0.4*VIN and 0.5*VIN is rather small, changing modes from the 80%/60% mode to the 75%/50% mode also will not ordinarily result in much wasted energy.

Figure 10:
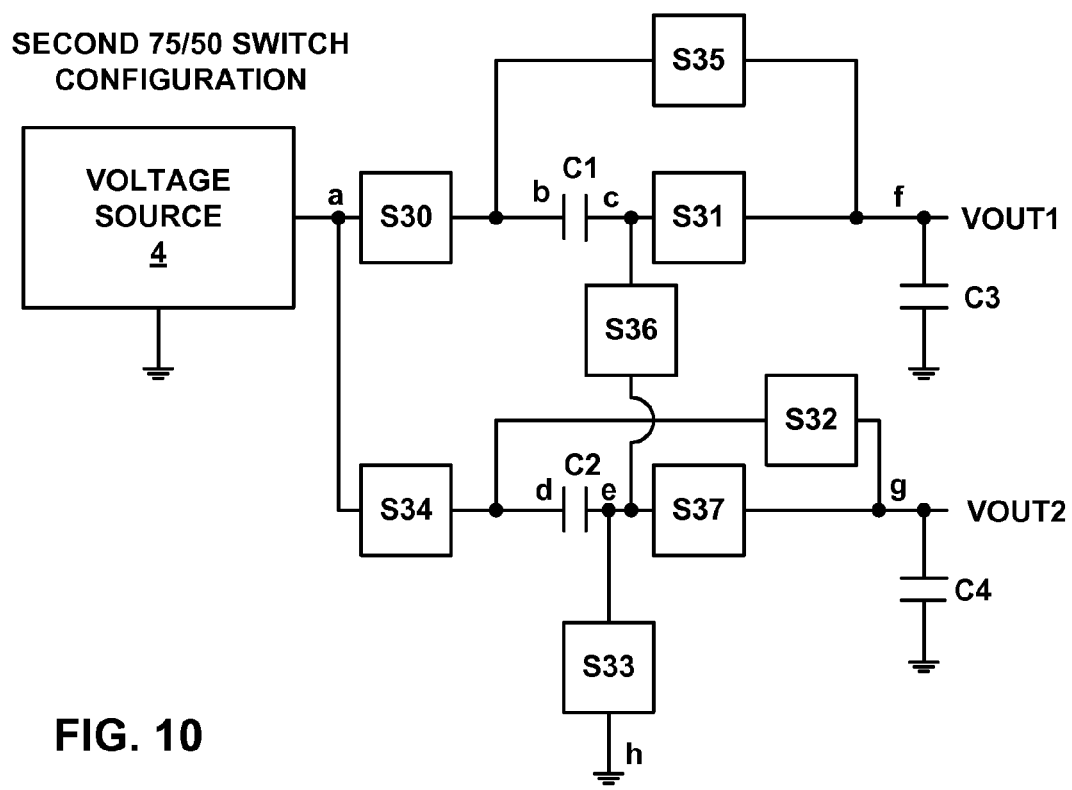
FIG. 10 is a circuit diagram illustrating a second switch configuration for the dc-dc converter of FIG. 1 configured for the 75%/50% conversion ratio mode.

FIG. 10 is a circuit diagram illustrating a second, alternative switch configuration for the dc-dc converter configured for the 75%/50% mode, which corresponds to the second row of Table 2. As indicated in Table 2, for a first, charge phase, nodes a and b are connected together, nodes c and f are connected together, and nodes d and g are connected together, and nodes e and h are connected together. For the charge phase, nodes a and b are connected together by toggling ON switch S30. Nodes c and f are connected together by toggling ON switch S31, nodes d and g are connected together by toggling ON switch S32, and nodes e and h are connected together by toggling ON switch S33. Switches S34-S37 are left open or toggled OFF such that no current can flow through them. Switches S30-S33 are the first set of switches that are toggled ON by switch controller 22 to transition to the charge phase. Toggling ON only switches S30-S33 generates the subcircuit associated with the charge phase for the second 75%/50% mode in the second row of Table 2.

For the pump phase, nodes a and d are connected together, nodes b and f are connected together, and nodes c, e, and g are connected together. For the pump phase, nodes a and d are connected together by toggling ON switch S34. Nodes b and f are connected together by toggling ON switch S35. Nodes c, e, and g are connected together by toggling ON switches S36 and S37. All other switches are left open or, in effect, toggled OFF. Switches S34-S37 are the second set of switches that are toggled ON by switch controller 22 to transition to the pump phase from the charge phase. Toggling ON only switches S34-S37 generates the subcircuit associated with the pump phase for the 75%/50% mode of the second row of Table 2.

As described above, FIGS. 9 and 10 show switch configurations within switch matrix 27 for the first 75%/50% conversion mode (first row of Table 2) and the second 75%/50a% conversion mode (second row of Table 2). Other switch configurations may be designed for the first and second 50%/25% conversion modes described in Table 2 based on arrangement of switch configurations in a manner similar to that shown and described with reference to FIGS. 9 and 10.

FIGS. 11A-11B are circuit diagrams illustrating subcircuits for the dc-dc converter configured for the first 75%/50% mode. FIG. 11A is the subcircuit generated during the charge phase for the first 75%/50% conversion mode. As shown in FIG. 11A, nodes a, b, and d are connected together, nodes c and f are connected together, and nodes e and g are connected together. Node h provides a common ground for VIN, VOUT1, and VOUT2. Otherwise stated, switches S22-S25 (FIG. 9) are toggled ON, and switches S26-S29 (FIG. 9) are toggled OFF.

With respect to FIG. 11A, using basic circuit calculation techniques during the charge phase, it is apparent that VOUT1 is equal to VIN minus the voltage drop across capacitor C1. As before, the voltage drop across capacitor C1 will be referred to as V1. VOUT2 is equal to VIN minus the voltage drop across capacitor C2. As before, the voltage drop across capacitor C2 will be referred to as V2. Therefore, during the charge phase, the following equations define the voltage levels at VOUT1 and VOUT2:

$$VOUT1=VIN-V1$$

$$VOUT2=VIN-V2$$

$$VOUT1+V1=VOUT2+V2$$

FIG. 11B is the subcircuit generated during the pump phase of the first 75%/50% mode. As shown in FIG. 11B, nodes b and f are connected together, nodes c, d, and g are connected together, and nodes e and h are connected together. Node h provides a common ground for VIN, VOUT1, and VOUT2. Otherwise stated, switches S26-S29 (FIG. 9) are toggled ON, and switches S22-S25 (FIG. 9) are toggled OFF. Note that the polarity of capacitor C1 is inverted in the pump phase compared to the charge phase. During the pump phase:

$$VOUT2=VOUT1+V1$$

$$VOUT2=V2$$

Based on the previous equations, the voltage levels of VOUT1 and VOUT2 can be calculated as just a function of VIN. Using basic algebra to solve the previous equations, VOUT1 equals 0.75*VIN and VOUT2 equals 0.5*VIN.

FIGS. 12A-12B are circuit diagrams illustrating subcircuits for the dc-dc converter configured for the second 75%/50% mode. FIG. 12A is the subcircuit generated during the charge phase for the second 75%/50% conversion mode. As shown in FIG. 12A, nodes a and b are connected together, nodes c and f are connected together, nodes d and g are connected together, and nodes e and h are connected together. Node h provides a common ground for VIN, VOUT1, and VOUT2. Otherwise stated, switches S30-S33 (FIG. 10) are toggled on, and switches S34-S37 (FIG. 10) are toggled off.

With respect to FIG. 12A, using basic circuit calculation techniques, during the charge phase, it is apparent that VOUT1 is equal to VIN minus the voltage drop across capacitor C1. As before, the voltage drop across capacitor C1 will be referred to as V1. VOUT2 is equal to VIN minus the voltage drop across capacitor C2. As before, the voltage drop across capacitor C2 will be referred to as V2. Therefore during the charge phase, the following equations define the voltage levels at VOUT1 and VOUT2:

$$VOUT1=VIN-V1$$

$$VOUT2=V2$$

FIG. 12B is the subcircuit generated during the pump phase. As shown in FIG. 12B, nodes a and d are connected together, nodes b and f are connected together, and nodes c, e, and g are connected together. Node h provides a common ground for VIN, VOUT1, and VOUT2. Otherwise stated, switches S34-S37 (FIG. 10) are toggled on, and switches S30-S33 (FIG. 10) are toggled off. During the pump phase:

$$VOUT1=VIN-V2+V1$$

$$VOUT2=VIN-V2$$

Based on the previous equations, the voltage levels of VOUT1 and VOUT2 can be calculated as just a function of VIN. Using basic algebra to solve the previous equations, VOUT1 equals 0.75*VIN and VOUT2 equals 0.5*VIN.

Table 2 describes switch configurations for two 50%/25% conversion modes. The switch configuration circuits for the two 50%/25% conversion modes can be designed based on the switch configurations described in Table 2.

As described in Table 1, dc-dc converter 6 may include a conversion mode for 80%/60% that requires three switching phases and two capacitors. However, conversion ratios of 0.8 and 0.6 also can be obtained with a dc-dc converter that requires two switching phases and three capacitors.

Figure 13:
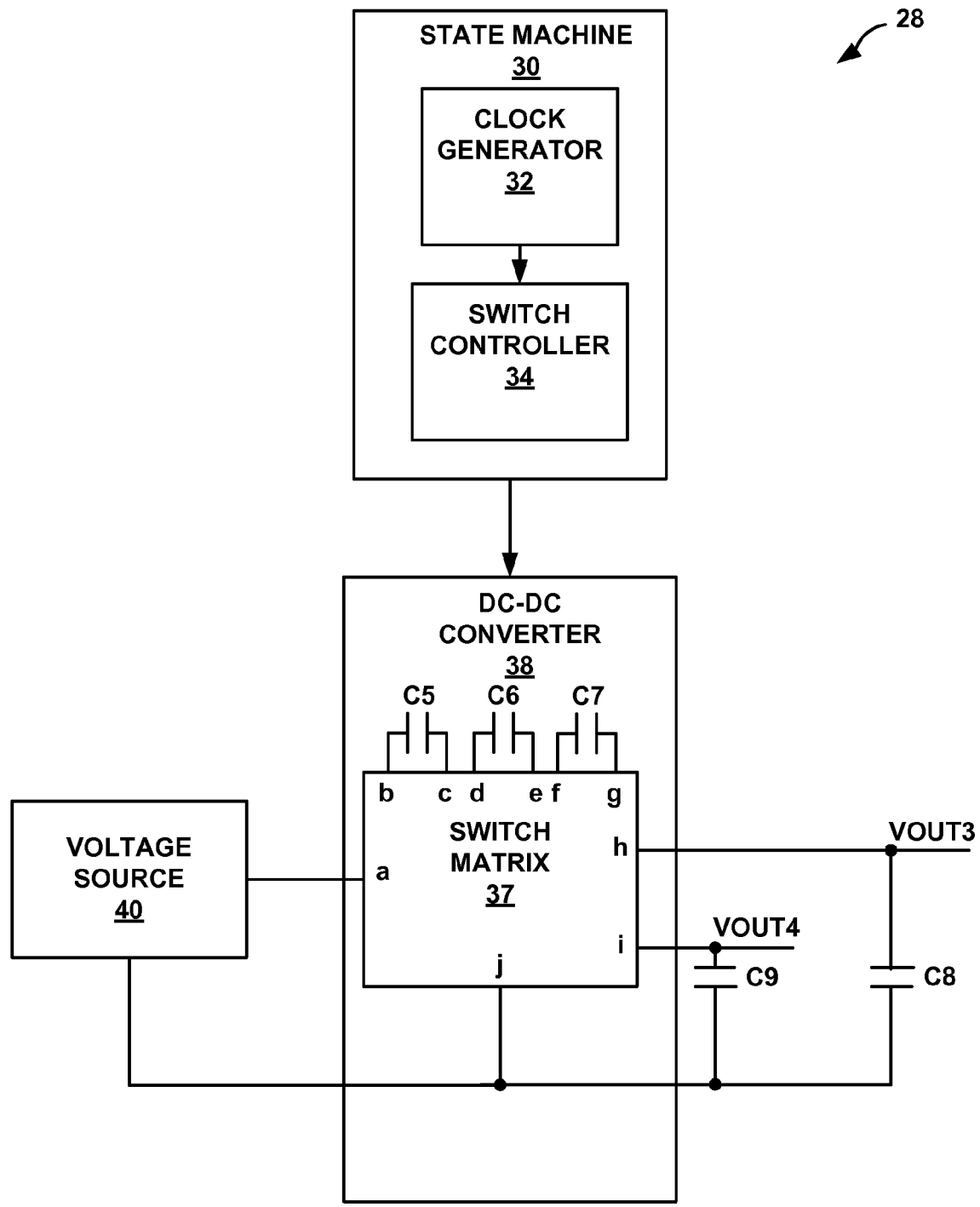
FIG. 13 is a block diagram illustrating an electrical system that includes a dc-dc converter with three capacitors.

FIG. 13 is a block diagram illustrating an electrical system 20 that includes a dc-dc converter 38 with three capacitors and two switch phases, i.e., a charge phase and a pump phase. As shown in FIG. 13, electrical system 20 includes a mode selection module 36, and a state machine 30 that comprises clock generator 32 and switch controller 34. State machine 30 may be substantially similar to state machine 8 (FIG. 2), and may be responsive to mode selection module 26 to control dc-dc converter 38 to select different modes via switch matrix 37. Clock generator 32 may be substantially similar to clock generator 14 (FIG. 2). Switch controller 34 may be substantially similar to switch controller 16 (FIG. 2). However, switch controller 34 only outputs signals to toggle switches within switch matrix 37 in two switching phases, instead of three switching phases like switch controller 16. As also shown in FIG. 13, electrical system 20 includes voltage source 40. Voltage source 40 may be substantially similar to voltage source 4 (FIG. 2).

As shown in FIG. 13, dc-dc converter 38 includes switch matrix 37 and capacitors C5, C6, and C7. As shown in FIG. 13, capacitors C5, C6, and C7 are external to switch matrix 37. However, in some implementations, capacitors C5, C6, and C7 may be internal to switch matrix 37. Switch matrix 37 includes a plurality of switches to interconnect nodes a-j. Voltage source 40 is coupled to node a of switch matrix 37. Node j provides a common ground. Capacitor C5 is coupled between nodes b and c, capacitor C6 is coupled between nodes d and e, and capacitor C7 is coupled between nodes f and g. Node h provides a first voltage output, VOUT3, and node i provides a second voltage output, VOUT4. Additionally as shown in FIG. 13, capacitor C8 is coupled between VOUT3 and the common ground, and capacitor C9 is coupled between VOUT4 and the common ground. The plurality of switches within switch matrix 37 may interconnect nodes a-j to transition between two switching phases. Table 3 defines the interconnection between nodes a-j for different switching phases to generate conversion ratios of approximately 0.8 and 0.6.

TABLE 3

| dc-dc conversion mode | Nodes that are interconnected within switch matrix 37 | | Conversion Ratio VOUT3/VIN | Conversion Ratio VOUT4/VIN |
|---|---|---|---|---|
| | Charge Phase | Pump Phase | | |
| 80%/60% | abdf, ceh, gi | bei, cf, dh, gj | 0.8 | 0.6 |

In one implementation, upon a rising or falling edge of a periodic wave provided by clock generator 32, switch controller 34 outputs a signal to dc-dc converter 38 to toggle switches within switch matrix 37 to connect nodes a, b, d, and f together, connect nodes c, e, and h together, and connect nodes g and i together. Upon a subsequent rising for falling edge of the periodic wave, switch controller 34 outputs a signal to dc-dc converter 38 to toggle switches within switch matrix 37 to connect nodes b, e, and i together, connect nodes c and f together, connect nodes d and h together, and connect nodes g and j together.

As described above with reference to Table 3, a dc-dc voltage conversion device having a set of first, second and third capacitors can output a first dc output voltage at a first output level different from the input level, and output a second dc output voltage at a second output level different from the input level at first and second output nodes, respectively. The set of capacitors may consist essentially of the three capacitors, which may be selectively arranged in at least two different subcircuits via a set of switches relative to the input node and the output nodes.

The switches may be controlled to transition between two phases comprising the two different subcircuits to convert the dc input voltage at the input level at the input node to the first output voltage at the first output level at the first output node and to the second output voltage at the second output level at the second output node. In particular, two outputs may be provided using three capacitors and two phases, with two corresponding subcircuits, and may be especially useful in producing outputs at levels of approximately 80% and 60%, respectively, of the input level.

Figure 14A:
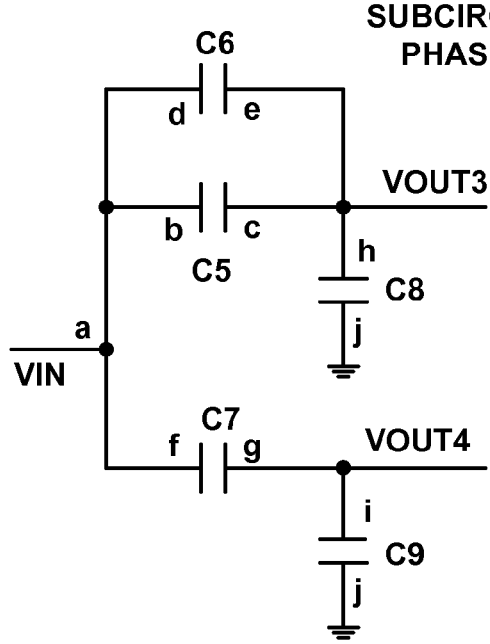
FIGS. 14A and 14B are circuit diagrams illustrating subcircuits for a dc-dc converter with three pump capacitors as shown in FIG. 13.
Figure 14B:
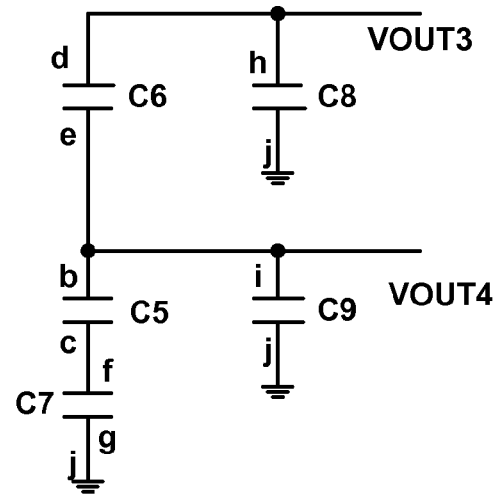

FIGS. 14A and 14B are subcircuit diagrams illustrating subcircuits for dc-dc converter 38 with three pump capacitors. FIG. 14A is the subcircuit generated during the charge phase for the 80%/60% conversion mode of dc-dc converter 38. As shown in FIG. 14A, nodes a, b, d, and f are connected together, nodes c, e, and h are connected together, and nodes g and i are connected together. Node j provides a common ground for VIN, VOUT3, and VOUT4. Using basic circuit calculation techniques, during the charge phase, it is apparent that VOUT3 is equal to VIN minus the voltage drop across capacitor C6 and VIN minus the voltage drop across C7. The voltage drop across capacitor C6 will be referred to as V6, and the voltage drop across capacitor C7 will be referred to as V7 herein. VOUT4 is equal to VIN minus V7. Therefore during the charge phase, the following equations define the voltage levels at VOUT3 and VOUT4:

$$VOUT3=VIN-V6$$

$$VOUT3=VIN-V5$$

$$VOUT4=VIN-V7$$

FIG. 14B is the subcircuit generated during the pump phase of the mode illustrated in Table 3. As shown in FIG. 14B, nodes b, e, and i are connected together, nodes c and f are connected together, nodes d and h are connected together, and nodes g and j are connected together. Node j provides a common ground for VIN, VOUT3, and VOUT4. None of capacitors C5, C6, and C7 are coupled to the input node, node a, in the subcircuit associated with the second switch phase, i.e., the pump phase. During the pump phase:

$$VOUT4=V5+V7$$

$$VOUT3=VOUT4+V6$$

Based on the previous equations, the voltage levels of VOUT3 and VOUT4 can be calculated as just a function of VIN. Using basic algebra to solve the previous equations, VOUT3 equals 0.8*VIN and VOUT4 equals 0.6*VIN.

Figure 15:
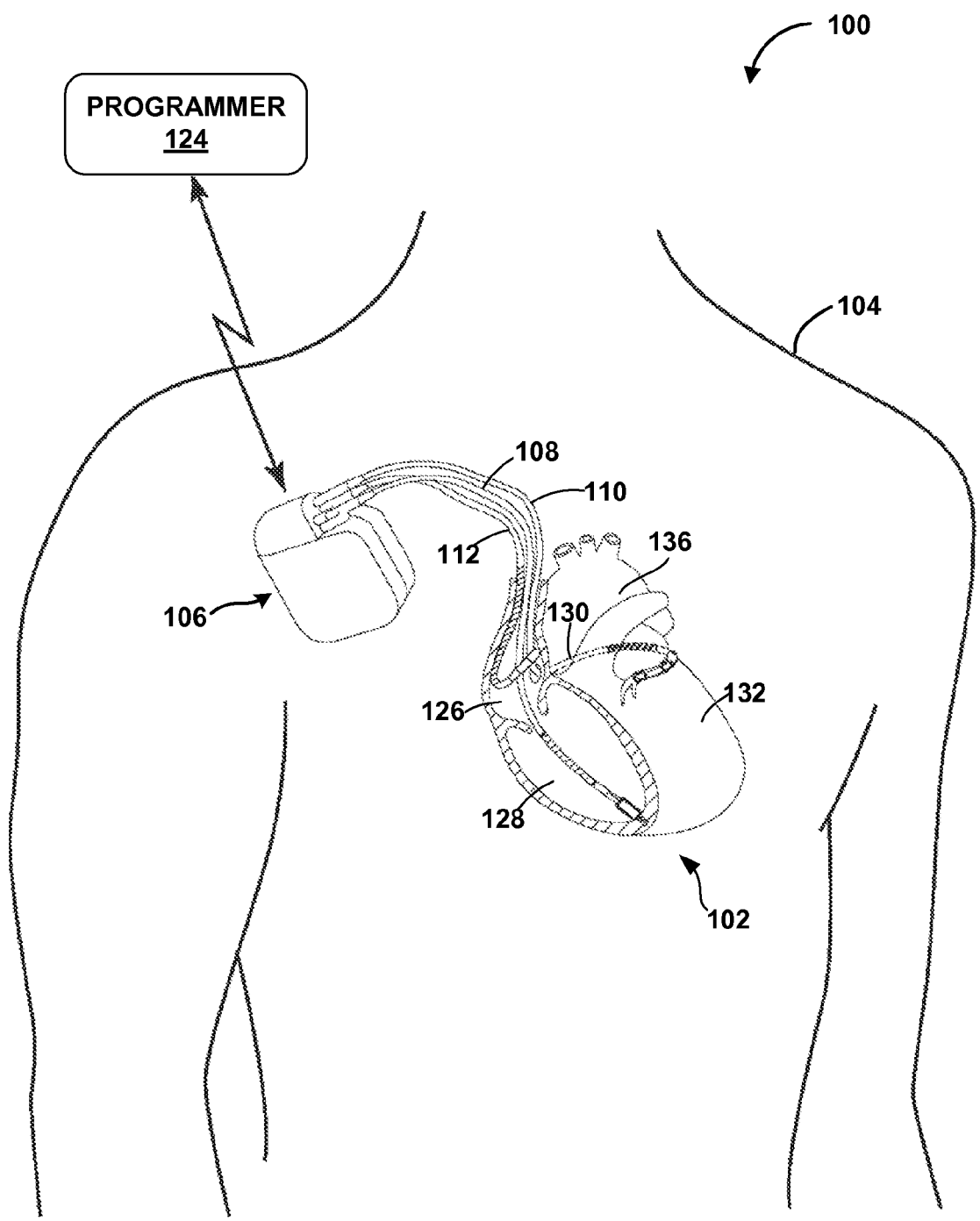
FIG. 15 is a conceptual diagram illustrating an implantable medical device suitable for incorporation of an electrical system with a dc-dc converter as described in this disclosure.

FIG. 15 is a conceptual diagram illustrating an implantable medical device suitable for incorporation of an electrical system with a dc-dc converter as described in this disclosure. As shown in FIG. 15, an example therapy system 100 provides therapy to heart 102 of a patient 104. Patient 104 ordinarily, but not necessarily, will be a human. Therapy system 100 includes an IMD 106, which is coupled to leads 108, 110, 112, and programmer 124. In the example of FIG. 15, IMD 106 may be, for example, an implantable pacemaker, cardioverter, and/or defibrillator that provides electrical stimulation signals to heart 12 via electrodes coupled to one or more of leads 108, 110, and 112.

In other applications, as an alternative to a cardiac therapy device, IMD 106 may take a variety of different forms such as an implantable spinal cord stimulator, gastric stimulator, deep brain stimulator, pelvic floor stimulator, functional electrical stimulator, cochlear stimulator, or the like. Alternatively, IMD 106 may be a sensing device or a therapeutic fluid delivery device, or a device that combines one or more of electrical stimulation, sensing and therapeutic fluid delivery structure and functionality. In each case, a dc-dc converter as described in this disclosure may be useful in converting a battery voltage level to one or more operating voltage levels for circuits or devices within the IMD.

Leads 108, 110, 112 extend into the heart 102 of patient 104 to sense electrical activity of heart 102 and/or deliver electrical stimulation to heart 102. In the example shown in FIG. 15, right ventricular (RV) lead 108 extends through one or more veins (not shown), the superior vena cava (not shown), and right atrium 126, and into right ventricle 128. Left ventricular (LV) coronary sinus lead 112 extends through one or more veins, the vena cava, right atrium 126, and into the coronary sinus 130 to a region adjacent to the free wall of left ventricle 132 of heart 102. Right atrial (RA) lead 112 extends through one or more veins and the vena cava, and into the right atrium 126 of heart 102.

IMD 196 may deliver electrical stimulation to heart 102 via one or more electrodes on any of implantable leads 108, 110, 112. One or more cardiac signals evoked by the stimulation tissue may be sensed via one or more electrodes on any of implantable leads 108, 110, 112. In some examples, IMD 106 may provide pacing pulses to heart 102 on a continuous basis or in response to the absence of an intrinsic pulse within heart 102.

Various configurations of electrodes used by IMD 106 for sensing and pacing may be unipolar or bipolar. In addition to pacing, IMD 106 may also provide defibrillation therapy and/or cardioversion therapy via electrodes located on at least one of the leads 108, 110, 112 and, more typically, via a combination of one or more elongated coil electrodes and another electrode, such as an electrode carried by a housing associated with IMD 106. A dc-dc conversion device as described in this disclosure may be incorporated in such an IMD housing with other circuitry or devices. The coil electrodes may be high voltage, high energy electrodes for delivery of cardioversion shocks and/or defibrillation shocks. IMD 106 may detect arrhythmia of heart 102, such as fibrillation of ventricles 128 and 132, and deliver defibrillation shock therapy to heart 102 in the form of high energy electrical pulses.

In some examples, external programmer 124 may be a handheld computing device, a computer workstation, or a home monitor device. Such devices may be configured to allow for one or more appropriate operations, including but not limited to the remote programming of IMD 106 and/or the remote retrieval of stored data. For example, programmer 124 may include a home monitor device connected to an off-site network device which may communicate with the home monitor device to program IMD 106 and/or retrieve data stored on IMD 106. In some cases, programmer 124 may be configured for wireless access to perform one or more functions, such as, programming of IMD 106, collection of sense data or operational data stored by IMD 106, and/or analysis of the stored data. Programmer 124 may include a user interface that receives input from and conveys output to a user, such as a clinician or patient.

Figure 16:
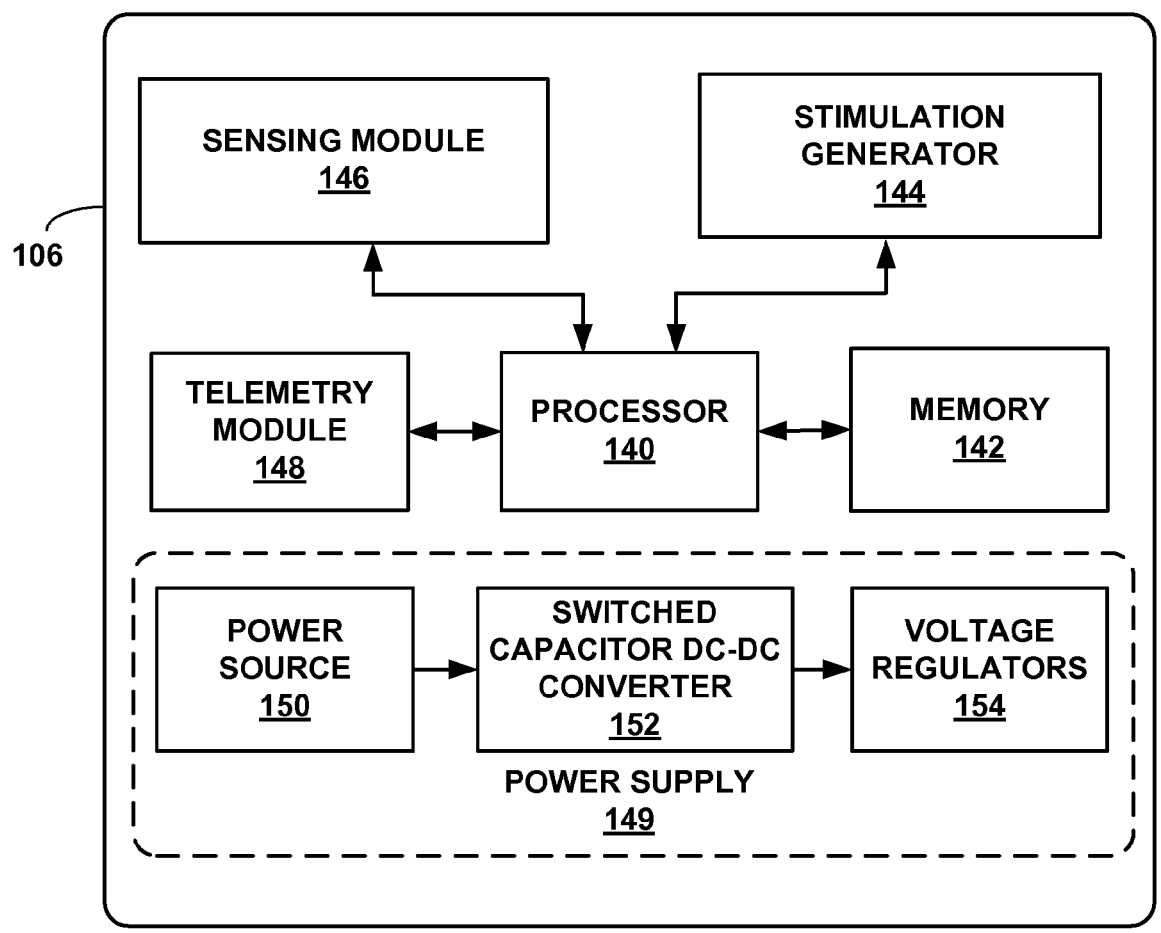
FIG. 16 is a block diagram of the implantable medical device of FIG. 15.

FIG. 16 is a functional block diagram of one example of IMD 106. IMD 106 is housed within an implantable medical device housing. Leads 108, 110, 112 are not shown in FIG. 16, but may be coupled to IMD 106. As shown in FIG. 16, IMD 106 may include a processor 140, memory 142, stimulation generator 144, sensing module 146, telemetry module 148, and a power supply 149 comprising a power source 150, switched capacitor dc-dc converter 152 and one or more voltage regulators 154 which may be considered to be medical device circuitry within the implantable medical device housing. Memory 142 includes computer-readable instructions that, when executed by processor 140, cause IMD 106 and processor 140 to perform various functions attributed to IMD 106 and processor 140 in this disclosure. Memory 142 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 142 may be a single memory module, or a combination of multiple memory modules including combinations of one or more types of memory as described above.

Processor 140 may include one or more of a microprocessor, a controller, a digital signal processor (DSP), an application specific integrated circuit (ASIC), a field-programmable gate array (FPGA), or equivalent discrete or integrated logic circuitry. In some examples, processor 140 may include multiple components, such as any combination of one or more microprocessors, one or more controllers, one or more DSPs, one or more ASICs, or one or more FPGAs, as well as other discrete or integrated logic circuitry. Accordingly, processor 140 may refer to a single processing and control unit, or a combination of processing and control units, in whatever form or combination, useful in controlling the functionality of IMD 106.

The functions performed by processor 140 may be realized by software, firmware, hardware or any combination thereof. Implantable stimulation generator 144 may be configured to deliver cardiac pacing stimulation to cardiac tissue via electrodes carried by one of more leads 108, 110, 112. Processor 140 controls stimulation generator 144 to deliver electrical stimulation therapy, such as pacing pulses and/or cardioversion/defibrillation shocks, to heart 102 according to a selected one or more of therapy programs, which may be stored in memory 142. Specifically, processor 140 may control stimulation generator 144 to deliver electrical pulses with amplitudes, pulse widths, frequency, or electrode polarities specified by the selected therapy programs.

In some examples, as described above, stimulation generator 144 delivers pacing, cardioversion, or defibrillation stimulation in the form of electrical pulses or shocks. In other examples, stimulation generator may deliver one or more of these types of stimulation in the form of other signals, such as sine waves, square waves, or other substantially continuous time signals. Stimulation generator 144 may include a switch module and processor 140 may use the switch module to select, e.g., via a data/address bus, electrodes to be used to deliver cardioversion-defibrillation shocks or pacing pulses. The switch module may include a switch array, switch matrix, multiplexer, or any other type of switching device suitable for selectively coupling stimulation energy to selected electrodes.

Sensing module 146 may be configured to monitor one or more signals from electrodes or other sensing devices. The sensed signals may be, for example, electrogram (EGM) signals or other signals, such as accelerometer, pressure, blood perfusion, respiratory, neurological or other physiological signals. Sensing module 146 may sense signals via electrodes or other sensing devices.

Telemetry module 148 may include any suitable hardware, firmware, software or any combination thereof for communicating with another device, such as programmer 124 (FIG. 15). Under the control of processor 140, telemetry module 148 may receive downlink telemetry from and send uplink telemetry to programmer 124 with the aid of an antenna, which may be internal and/or external. Processor 140 may provide the data to be uplinked to programmer 124 and the control signals for the telemetry circuit within telemetry module 148, e.g., via an address/data bus. In some examples, telemetry module 148 may provide received data to processor 140 via a multiplexer.

The various components of IMD 106 may be coupled to power supply 149, which may include power source 150, switched capacitor dc-dc converter 152, and one or more voltage regulators 154. Power source 150 may comprise a rechargeable or nonrechargeable battery that provides an input voltage for switched capacitor dc-dc converter 152. The dc-dc converter 152 upconverts or downconverts the level of the input voltage to one or more output voltage levels for one or more voltage regulators 154.

Voltage regulators 154 regulate the one or more output voltages from switched capacitor dc-dc converter 152 to provide an operational power level or levels for use within IMD 106. A non-rechargeable battery may be selected to last for several years, while a rechargeable battery may be inductively charged from an external device, e.g., on a daily or weekly basis. In either case, dc-dc converter 152 may be configured as described in this disclosure to provide one or more output voltage levels in either two capacitor, three phase modes or three capacitor, two phase modes. Hence, IMD 106 and, more particularly power supply 149 may include a dc-dc converter consistent with any of the wide variety of implementation examples described in this disclosure.

Figure 17:
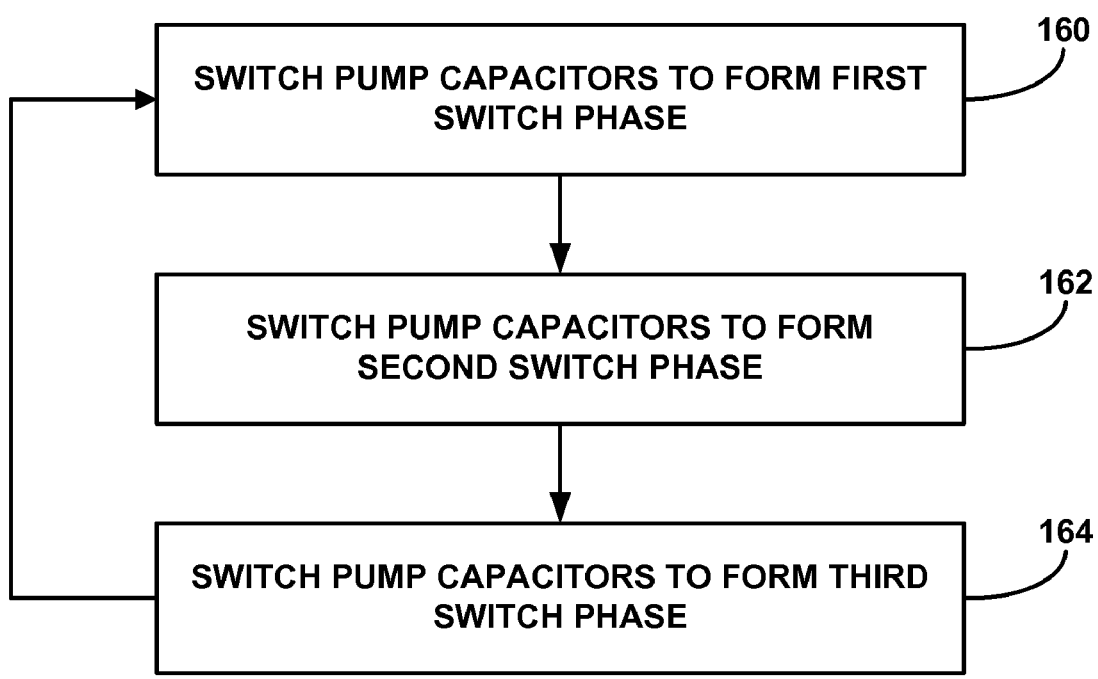
FIG. 17 is a flow diagram illustrating three-phase operation of an example dc-dc converter as described in this disclosure.

FIG. 17 is a flow diagram illustrating three-phase operation of an example dc-dc converter as described in this disclosure. As shown in FIG. 17, the dc-dc converter, e.g., dc-dc converter 6 or 27, switches a plurality of pump capacitors in an arrangement to form a first switch phase (160). The first switch phase may be formed using two pump capacitors, C1 and C2, e.g., as described with reference to Table 1. Transition to the first switch phase may be responsive to a rising or falling edge of a clock signal, and may be controlled by a state machine, e.g., such as state machine 8 or 19.

Upon entering the first switch phase, in response to the next clock signal (e.g., rising or falling edge), the dc-dc converter may switch the pump capacitors such that the capacitors form a second switch phase (162). Again, the second switch phase may be formed with two pump capacitors in the manner described with reference to Table 1. In response to the next clock signal, the dc-dc converter may transition from the second switch phase to the third switch phase. In particular, the dc-dc converter may switch the pump capacitors as described with reference to Table 1 (164). In response to the next clock signal, the dc-dc converter may restart the process by switching the pump capacitors to form the first switch phase. In other words, capacitors C1 and C2 are arranged in at least three different subcircuits in at least three different phases to convert the input voltage to possibly two output voltages.

Although FIG. 17 shows an example in which the dc-dc converter transitions from the first switch phase, to the second switch phase, and then to the third switch phase, an alternative ordering may be used. For example, the dc-dc converter could transition from the first switch phase to the third switch phase and then to the second switch phase, or from the third switch phase to the second switch phase and then to the first switch phase. In each case, the dc-dc converter is configured to transition between three different phases with three different subcircuits formed by the pump capacitors in combination with the switches and other circuit elements of the dc-dc converter. A three-phase dc-dc converter may permit realization of a variety of conversion ratios. In addition, in various implementations, such conversion ratios may be achieved with a relatively small number of pump capacitors, such as two pump capacitors.

Figure 18:
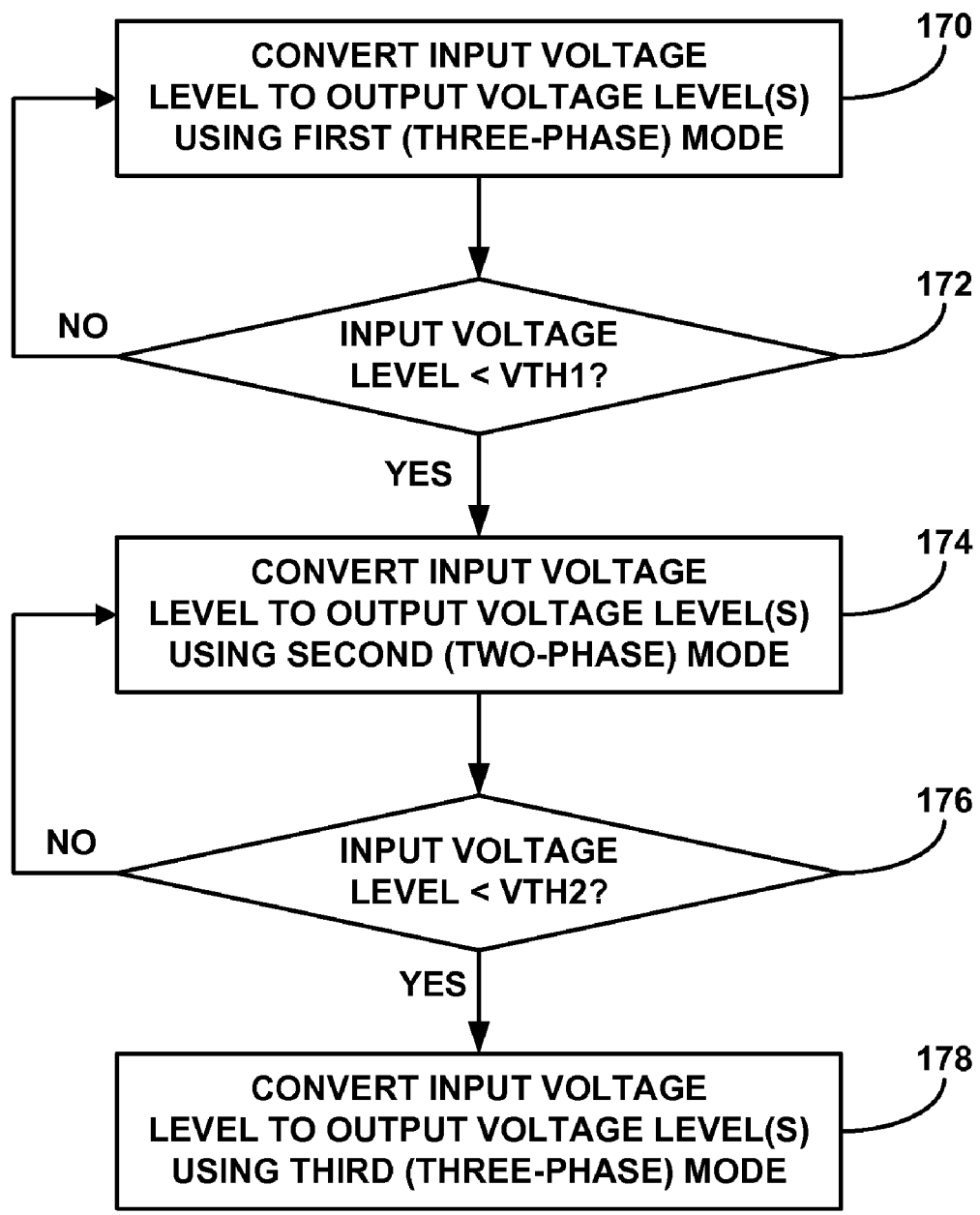
FIG. 18 is a flow diagram illustrating multi-mode operation of an example dc-dc converter as described in this disclosure.

FIG. 18 is a flow diagram illustrating multi-mode operation of an example dc-dc converter as described in this disclosure. In the example of FIG. 18, a dc-dc converter (e.g., dc-dc converter 6 or 38) may work in conjunction with a mode selection module (e.g., mode selection module 5 or 36) to transition between different conversion ratio modes and, in some cases, different dc-dc conversion modes (e.g., two-phase versus three-phase modes). As shown in FIG. 18, a dc-dc converter may converter an input voltage level to one or more output voltage levels using a first mode (170). In some implementations, the first mode may be a three-phase mode, such as a two pump capacitor, three-phase mode as described with reference to Table 1.

If the input voltage level does not fall below (i.e., is not less than) a first threshold voltage $VTH1$ (e.g., 3.2 V in the case of a nominal 3.3 V battery as a voltage source) (172), the dc-dc converter may continue to operate in the first mode (170). If the input voltage falls below the first threshold voltage $VTH1$ (172), however, the dc-dc converter may transition to a second mode (174). In particular, the dc-dc converter may convert the input voltage level to one or more output voltage levels using the second mode (174). The second mode, in some implementations may be a two-phase mode, such as a two pump capacitor, two-phase mode as described with reference to Table 2.

While the input voltage level remains greater than a second threshold voltage $VTH2$ (176), the dc-dc converter continues to convert the input voltage level to one or more output voltage level using the second mode (174). As one example, the $VTH2$ level could be 2.5 V in the case of a battery as voltage source. If the input voltage level is less than the second threshold voltage $VTH2$ (176), the dc-dc converter may transition to a third mode (178). In particular, the dc-dc converter then may convert the input voltage level to one or more output voltage levels using the third mode (178). In some implementations, the third mode may be a two-capacitor, three-phase mode, such as those described with reference to Table 1.

As shown in FIG. 18, the dc-dc converter may transition from a three-phase mode for higher input voltage levels, to a two-phase mode for intermediate input voltage levels, and then a three-phase mode for lower input voltage levels. In general, the first mode (170) may have a lower conversion ratio, such as 60%/40%, the second mode may have a higher conversion ratio than the first mode, such as 75%/50%, and the third mode may have a higher conversion ratio than the second mode, such as 80%/60%. In each mode, the dc-dc converter may transition between different phases.

In a three-phase mode, the dc-dc converter may transition between first, second, and third switch phases, in that order or another order. In a two-phase mode, the dc-dc converter may transition between charge and pump phases. In some implementations, the first or third mode may be a three pump capacitor, two-phase mode, e.g., as described with reference to Table 3. For example, in some implementations, instead of a three-phase mode, the mode may be a three pump capacitor, two-phase 80%/60% conversion ratio mode as described with reference to Table 3. In each of the two-phase and three-phase modes, the dc-dc converter may make use of a mode selection module, state machine, switching matrix, and other related components as described in this disclosure.

Although FIG. 18 shows comparison of an input voltage VIN to one or more threshold values by mode selection module 24 for purposes of selecting different conversion ratio modes, in some implementations, one or both of VOUT1 and VOUT2 may be compared to applicable thresholds, where such comparison is used by mode selection module 24 as the basis for selecting different conversion ratio modes. Accordingly, comparison of VIN to threshold values in FIG. 18 is presented for purposes of illustration and should not be considered limiting of the techniques for multi-mode selection as broadly described in this disclosure. Rather, the disclosure contemplates a variety of comparisons or determinations for the purpose of selecting different conversion ratio modes in a multi-mode switched capacitor dc-dc converter.

Various implementation examples have been described. These and other implementations are within the scope of the following claims.

The invention claimed is:

1. A dc-dc voltage conversion device comprising:
an input node to receive a dc input voltage at an input level;
an output node to output a dc output voltage at an output level;
a first pump capacitor and a second pump capacitor;
switches configured to selectively arrange only the first and second pump capacitors in different subcircuits relative to the input node and the output node; and
a controller configured to control the switches to transition between a first number of phases comprising a first set of the subcircuits in a first conversion mode comprising a first conversion ratio, and between a second number of phases comprising a second set of subcircuits in a second conversion mode comprising a second conversion ratio, to convert the input voltage to the output voltage, wherein the first number of phases is at least three, the output level is different from the input level, and the first conversion ratio is different than the second conversion ratio, and wherein the first conversion ratio comprises a ratio of the output level to the input level and comprises at least one of 83%, 80%, 60%, 40%, 20%, or 17%.

2. The device of claim 1, wherein the first and second numbers are the same.

3. The device of claim 1, wherein the first and second numbers are different.

4. The device of claim 1, further comprising a third capacitor coupled between the output node and a reference, wherein the output voltage is generated across the third capacitor, wherein each of the subcircuits in the first set of the subcircuits and in the second set of the subcircuits comprises a set of capacitors consisting essentially of the first pump capacitor, the second pump capacitor, and the third capacitor.

5. The device of claim 1, wherein:
the output node comprises a first output node to output a first output voltage at a first output level, and a second output node to output a second output voltage at a second output level different from the first output level,
the subcircuits are configured to convert the input voltage to the first output voltage at the first output level at the first output node and to the second output voltage at the second output level at the second output node.

6. The device of claim 5, wherein the controller is configured to control the switches in the first conversion mode such that a ratio x of the first output level to the input level and a ratio y of the second output level to the input level, represented as a percentage value, is one of x/y equal to approximately 80%/60%, 83%/50%, 80%/40%, 60%/40%, 60%/20%, or 40%/20%, and in the second conversion mode such that the ratio x of the first output level to the input level and a ratio y of the second output level to the input level, represented as a percentage value, is one of x/y equal to approximately 75%/50% or 50%/25%.

7. The device of claim 5, wherein the controller is configured to control the switches in the first conversion mode such that a ratio x of the first output level to the input level and a ratio y of the second output level to the input level, represented as a percentage value, is x/y approximately equal to 80%/60%, and in the second conversion mode such that a ratio x of the first output level to the input level and a ratio y of the second output level to the input level, represented as a percentage value, is x/y approximately equal to 75%/50%.

8. The device of claim 5, further comprising:
a third capacitor coupled between the first output node and a reference, wherein the first output voltage is generated across the third capacitor; and
a fourth capacitor coupled between the first output node and the reference, wherein the second output voltage is generated across the fourth capacitor,
wherein each of the subcircuits in the first set of the subcircuits and in the second set of the subcircuits comprises a set of capacitors consisting essentially of the first pump capacitor, the second pump capacitor, and the third and fourth capacitors.

9. The device of claim 5, wherein the first number of phases is three and the second number of phases is two, and wherein the controller is configured to control the switches to transition between the phases in response to a clock signal.

10. The device of claim 1, further comprising a mode selection module that selects one of the first and second conversion modes based on the input level.

11. The device of claim 10, wherein the first number of phases is greater than the second number of phases, and the mode selection module is configured to select the first conversion mode when the input level is greater than a first threshold voltage level, and to select the second conversion mode when the input level is less than the first threshold voltage level.

12. The device of claim 11, wherein the controller is configured to control the switches to transition between the first number of phases comprising a third set of the subcircuits in a third conversion mode, wherein the mode selection module selects the second conversion mode when the input level is less than the first threshold voltage level and greater than a second threshold voltage level, and selects the third conversion mode when the input level is less than the second threshold voltage level, wherein the first, second and third sets of subcircuits are different from one another.

13. A dc-dc voltage conversion method comprising:
receiving, at an input node, a dc input voltage at an input level;
outputting, at an output node, a dc output voltage at an output level different from the input level; and
selectively arranging only first and second pump capacitors in different subcircuits relative to the input node and the output node to transition between a first number of phases comprising a first set of the subcircuits in a first conversion mode comprising a first conversion ratio, and between a second number of phases comprising a second set of subcircuits in a second conversion mode comprising a second conversion ratio, to convert the input voltage to the output voltage, wherein the first number of phases is at least three, the output level is different from the input level, and the first conversion ratio is different than the second conversion ratio, and wherein the first conversion ratio comprises a ratio of the output level to the input level and comprises at least one of 83%, 80%, 60%, 40%, 20%, or 17%.

14. The method of claim 13, wherein the first and second numbers are the same.

15. The method of claim 13, wherein the first and second numbers are different.

16. The method of claim 13, further comprising generating the output voltage across a third capacitor coupled between the output node and a reference, wherein each of the subcircuits in the first set of the subcircuits and in the second set of the subcircuits comprises a set of capacitors consisting essentially of the first pump capacitor, the second pump capacitor, and the third capacitor.

17. The method of claim 13, wherein the output node comprises first and second output nodes, and wherein outputting the output voltage comprises:
outputting, at the first output node, a first dc output voltage at a first output level different from the input level; and
outputting, at the second output node, a second dc output voltage at a second output level different from the input level,
wherein the second output level is different from the first output level, and
wherein the subcircuits are configured to convert the input voltage to the first output voltage at the first output level at the first output node and to the second output voltage at the second output level at the second output node.

18. The method of claim 17, further comprising arranging the capacitors in the subcircuits in the first conversion mode such that a ratio x of the first output level to the input level and a ratio y of the second output level to the input level, represented as a percentage value, is one of x/y equal to approximately 80%/60%, 83%/50%, 80%/40%, 60%/40%, 60%/20%, or 40%/20% and in the second conversion mode such that the ratio x of the first output level to the input level and a ratio y of the second output level to the input level, represented as a percentage value, is one of x/y equal to approximately 75%/50% or 50%/25%.

19. The method of claim 17, further comprising arranging the capacitors in the subcircuits in the first conversion mode such that a ratio x of the first output level to the input level and a ratio y of the second output level to the input level, represented as a percentage value, is x/y approximately equal to 80%/60%, and in the second conversion mode such that a ratio x of the first output level to the input level and a ratio y of the second output level to the input level, represented as a percentage value, is x/y approximately equal to 75%/50%.

20. The method of claim 17, further comprising:
generating the first output voltage across a third capacitor coupled between the first output node and a reference; and
generating the second output voltage across a fourth capacitor coupled between the first output node and the reference,
wherein each of the subcircuits in the first set of the subcircuits and in the second set of the subcircuits comprises a set of capacitors consisting essentially of the first pump capacitor, the second pump capacitor, and the third and fourth capacitors.

21. The method of claim 17, wherein the first number of phases is three and the second number of phases is two, and wherein arranging the capacitors comprises arranging the capacitors via switches, the method further comprising controlling the switches to transition between phases in response to a clock signal.

22. The method of claim 13, further comprising selecting one of the first and second conversion modes based on the input level.

23. The method of claim 22, wherein the first number of phases is greater than the second number of phases, the method further comprising selecting the first conversion mode when the input level is greater than a first threshold voltage level, and selecting the second conversion mode when the input level is less than the first threshold voltage level.

24. The method of claim 23, further comprising selectively arranging the capacitors in different subcircuits relative to the input node and the output node to transition between the first number of phases comprising a third set of the subcircuits in a third conversion mode, wherein selecting one of the first and second conversion modes comprises selecting the second conversion mode when the input level is less than the first threshold voltage level and greater than a second threshold voltage level, and selecting the third conversion mode when the input level is less than the second threshold voltage level, wherein the first, second and third sets of subcircuits are different from one another.

25. A dc-dc voltage conversion device comprising:
means for receiving, at an input node, a dc input voltage at an input level;
means for outputting, at an output node, a dc output voltage at an output level different from the input level; and
means for selectively arranging only first and second pump capacitors in different subcircuits relative to the input node and the output node to transition between a first number of phases comprising a first set of the subcircuits in a first conversion mode comprising a first conversion ratio, and between a second number of phases comprising a second set of subcircuits in a second conversion mode comprising a second conversion ratio, to convert the input voltage to the output voltage,
wherein the first number of phases is at least three, the output level is different from the input level, and the first conversion ratio is different than the second conversion ratio, and wherein the first conversion ratio comprises a ratio of the output level to the input level and comprises at least one of 83%, 80%, 60%, 40%, 20%, or 17%.

26. The device of claim 25, wherein the first and second numbers are the same.

27. The device of claim 25, wherein the first and second numbers are different.

28. The device of claim 25, further comprising means for generating the output voltage across a third capacitor coupled between the output node and a reference, wherein each of the subcircuits in the first set of the subcircuits and in the second set of the subcircuits comprises a set of capacitors consisting essentially of the first pump capacitor, the second pump capacitor, and the third capacitor.

29. The device of claim 25, wherein the output node comprises first and second output nodes, and wherein the means for outputting the output voltage comprises:
means for outputting, at the first output node, a first dc output voltage at a first output level different from the input level; and
means for outputting, at the second output node, a second dc output voltage at a second output level different from the input level,
wherein the second output level is different from the first output level, and wherein the subcircuits are configured to convert the input voltage to the first output voltage at the first output level at the first output node and to the second output voltage at the second output level at the second output node.

30. The device of claim 29, further comprising means for arranging the capacitors in the subcircuits in the first conversion mode such that a ratio x of the first output level to the input level and a ratio y of the second output level to the input level, represented as a percentage value, is one of x/y equal to approximately 80%/60%, 83%/50%, 80%/40%, 60%/40%, 60%/20%, or 40%/20% and in the second conversion mode such that the ratio x of the first output level to the input level and a ratio y of the second output level to the input level, represented as a percentage value, is one of x/y equal to approximately 75%/50% or 50%/25%.

31. The device of claim 29, further comprising means for arranging the capacitors in the subcircuits in the first conversion mode such that a ratio x of the first output level to the input level and a ratio y of the second output level to the input level, represented as a percentage value, is x/y approximately equal to 80%/60%, and in the second conversion mode such that a ratio x of the first output level to the input level and a ratio y of the second output level to the input level, represented as a percentage value, is x/y approximately equal to 75%/50%.

32. The device of claim 31, further comprising:
means for generating the first output voltage across a third capacitor coupled between the first output node and a reference; and
means for generating the second output voltage across a fourth capacitor coupled between the first output node and the reference,
wherein each of the subcircuits in the first set of the subcircuits and in the second set of the subcircuits comprises a set of capacitors consisting essentially of the first pump capacitor, the second pump capacitor, and the third and fourth capacitors.

33. The device of claim 31, wherein the first number of phases is three and the second number of phases is two, the device further comprising means for selecting one of the first and second conversion modes based on the input level, wherein the first number of phases is greater than the second number of phases, the device further comprising means for selecting the first conversion mode when the input level is greater than a first threshold voltage level, and selecting the second conversion mode when the input level is less than the first threshold voltage level, wherein the first and second sets of subcircuits are different from one another.

34. An implantable medical device comprising:
an implantable medical device housing;
medical device circuitry within the housing;
a battery, within the housing, that generates a dc input voltage; and
a dc-dc voltage conversion device, within the housing, comprising:
an input node to receive the dc input voltage at an input level;
an output node to output a dc output voltage at an output level;
a first pump capacitor and a second pump capacitor;
switches configured to selectively arrange only the first and second pump capacitors in different subcircuits relative to the input node and the output node; and
a controller configured to control the switches to transition between a first number of phases comprising a first set of the subcircuits in a first conversion mode comprising a first conversion ratio, and between a second number of phases comprising a second set of subcircuits in a second conversion mode comprising a second conversion ratio, to convert the input voltage to the output voltage,
wherein the first number of phases is at least three, the output level is different from the input level, and the first conversion ratio is different than the second conversion ratio, and wherein the first conversion ratio comprises a ratio of the output level to the input level and comprises at least one of 83%, 80%, 60%, 40%, 20%, or 17%.

35. The implantable medical device of claim 34, wherein the first and second numbers are the same.

36. The implantable medical device of claim 34, wherein the first and second numbers are different.

37. The device of claim 34,
wherein, the output node comprises a first output node to output a first dc output voltage at a first output level different from the input level, and a second output node to output a second dc output voltage at a second output level different from the input level,
wherein the second output level is different from the first output level,
wherein the subcircuits are configured to convert the dc input voltage at the input level at the input node to the first dc output voltage at the first output level at the first output node and to the second dc output voltage at the second output level at the second output node, and
wherein the controller is configured to control the switches in the first conversion mode such that a ratio x of the first output level to the input level and a ratio y of the second output level to the input level, represented as a percentage value, is one of x/y equal to approximately 80%/60%, 83%/50%, 80%/40%, 60%/40%, 60%/20%, or 40%/20%, and in the second conversion mode such that the ratio x of the first output level to the input level and a ratio y of the second output level to the input level, represented as a percentage value, is one of x/y equal to approximately 75%/50% or 50%/25%.

38. The device of claim 34, further comprising:
a third capacitor coupled between the first output node and a reference, wherein the first output voltage is generated across the third capacitor; and
a fourth capacitor coupled between the first output node and the reference, wherein the second output voltage is generated across the fourth capacitor,
wherein each of the subcircuits in the first set of the subcircuits and in the second set of the subcircuits comprises a set of capacitors consisting essentially of the first pump capacitor, the second pump capacitor, and the third and fourth capacitors.

39. The device of claim 34, further comprising a mode selection module that selects one of the first and second conversion modes based on the input level.

40. A dc-dc voltage conversion device comprising:
an input node to receive a dc input voltage at an input level;
a first output node to output a dc output voltage at a first output level different from the input level;
a second output node to output a dc output voltage at a second output level different from the input level;
a first pump capacitor and a second pump capacitor;
switches configured to selectively arrange only the first and second pump capacitors in different subcircuits relative to the input node and the first and second output nodes; and a controller configured to control the switches to transition between a first number of phases comprising a first set of the subcircuits in a first conversion mode comprising a first conversion ratio, and between a second number of phases comprising a second set of subcircuits in a second conversion mode comprising a second conversion ratio, to convert the input voltage to the output voltage, wherein the first number of phases is at least three, and the first conversion ratio is different than the second conversion ratio, and wherein in the first conversion mode a ratio x of the first output level to the input level and a ratio y of the second output level to the input level, represented as a percentage value, is one of x/y equal to approximately 80%/60%, 83%/50%, 67%/50%, 80%/40%, 75%/25%, 60%/40%, 60%/20%, 50%/33%, 50%/17%, or 40%/20%, and in the second conversion mode the ratio x of the first output level to the input level and the ratio y of the second output level to the input level, represented as a percentage value, is one of x/y equal to approximately 75%/50% or 50%/25%.

41. A dc-dc voltage conversion method comprising:
receiving, at an input node, a dc input voltage at an input level;
outputting, at a first output node, a dc output voltage at a first output level different from the input level;
outputting, at a second output node, a dc output voltage at a second output level different from the input level and different from the first output level; and
selectively arranging only first and second pump capacitors in different subcircuits relative to the input node and the first and second output nodes to transition between a first number of phases comprising a first set of the subcircuits in a first conversion mode comprising a first conversion ratio, and between a second number of phases comprising a second set of subcircuits in a second conversion mode comprising a second conversion ratio, to convert the input voltage to the first and second output voltages, wherein the first number of phases is at least three, and the first conversion ratio is different than the second conversion ratio, and wherein in the first conversion mode a ratio x of the first output level to the input level and a ratio y of the second output level to the input level, represented as a percentage value, is one of x/y equal to approximately 80%/60%, 83%/50%, 67%/50%, 80%/40%, 75%/25%, 60%/40%, 60%/20%, 50%/33%, 50%/17%, or 40%/20%, and in the second conversion mode the ratio x of the first output level to the input level and the ratio y of the second output level to the input level, represented as a percentage value, is one of x/y equal to approximately 75%/50% or 50%/25%.

* * * * *